(12) United States Patent
Osypka

(10) Patent No.: US 8,137,317 B2
(45) Date of Patent: *Mar. 20, 2012

(54) LOCKING VASCULAR INTRODUCER ASSEMBLY WITH ADJUSTABLE HEMOSTATIC SEAL

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 788 days.

This patent is subject to a terminal disclaimer.

(21) Appl. No.: 10/940,415

(22) Filed: Sep. 14, 2004

(65) Prior Publication Data

US 2005/0090779 A1    Apr. 28, 2005

Related U.S. Application Data

(63) Continuation-in-part of application No. 10/389,229, filed on Mar. 14, 2003, now Pat. No. 7,192,433.

(60) Provisional application No. 60/364,649, filed on Mar. 15, 2002, provisional application No. 60/391,793, filed on Jun. 27, 2002.

(51) Int. Cl.
*A61M 5/178* (2006.01)

(52) U.S. Cl. .............. 604/164.05; 604/167.03

(58) Field of Classification Search ............ 604/459.5, 604/198, 158–170.03, 104–109, 246–248, 604/264, 533–535; 206/459.5; 606/108
See application file for complete search history.

(56) References Cited

U.S. PATENT DOCUMENTS

| | | | |
|---|---|---|---|
| 3,653,388 A | 4/1972 | Tenckhoff | |
| 4,166,469 A | 9/1979 | Littleford | |
| 4,243,050 A | 1/1981 | Littleford | |
| 4,345,606 A | 8/1982 | Littleford | |
| 4,362,156 A | 12/1982 | Feller, Jr. et al. | |
| 4,451,256 A | 5/1984 | Weikl et al. | |
| RE31,855 E | 3/1985 | Osborne | |
| 4,581,025 A | 4/1986 | Timmermans | |
| 4,596,559 A | 6/1986 | Fleischhacker | |
| 4,772,266 A * | 9/1988 | Groshong | 604/164.05 |
| 4,886,507 A * | 12/1989 | Patton et al. | 604/284 |
| 4,983,168 A | 1/1991 | Moorehead | |
| 5,059,186 A * | 10/1991 | Yamamoto et al. | 604/537 |
| 5,125,904 A | 6/1992 | Lee | |
| 5,125,915 A | 6/1992 | Berry et al. | |
| 5,141,497 A * | 8/1992 | Erskine | 604/164.05 |
| 5,250,033 A * | 10/1993 | Evans et al. | 604/160 |
| 5,409,463 A | 4/1995 | Thomas et al. | |
| 5,409,469 A | 4/1995 | Schaerf | |
| 5,441,504 A | 8/1995 | Pihndorf et al. | |
| 5,536,255 A | 7/1996 | Moss | |

(Continued)

FOREIGN PATENT DOCUMENTS

WO    WO 01/49363 A1    7/2001

*Primary Examiner* — Matthew F Desanto
(74) *Attorney, Agent, or Firm* — Scott D. Wofsy; Edwards Wildman Palmer LLP

(57) ABSTRACT

A vascular introducer assembly is disclosed that includes a dilator, a sheath having an axial lumen for accommodating the dilator, a locking collar for securing the dilator and the sheath to one another and an adjustable hemostatic seal for preventing fluid egress from the axial lumen and restricting insertion of instruments through the axial lumen before and after the dilator is separated from the vascular introducer.

27 Claims, 19 Drawing Sheets

U.S. PATENT DOCUMENTS

| | | |
|---|---|---|
| 5,713,867 A | 2/1998 | Morris |
| 5,741,233 A | 4/1998 | Riddle et al. |
| 5,755,693 A * | 5/1998 | Walker et al. ............. 604/160 |
| 5,827,296 A | 10/1998 | Morris et al. |
| 5,871,530 A | 2/1999 | Williams et al. |
| 5,951,518 A | 9/1999 | Licata et al. |
| 6,038,472 A | 3/2000 | Williams et al. |
| 6,178,355 B1 | 1/2001 | Williams et al. |
| 6,336,914 B1 | 1/2002 | Gillespie, III |
| 6,595,946 B1 * | 7/2003 | Pasqualucci ............. 604/27 |
| 6,623,460 B1 * | 9/2003 | Heck ............. 604/256 |
| 6,641,564 B1 * | 11/2003 | Kraus ............. 604/164.1 |
| 2002/0010436 A1 | 1/2002 | Becket et al. |
| 2004/0267202 A1 * | 12/2004 | Potter ............. 604/158 |
| 2006/0149293 A1 * | 7/2006 | King et al. ............. 606/108 |

* cited by examiner

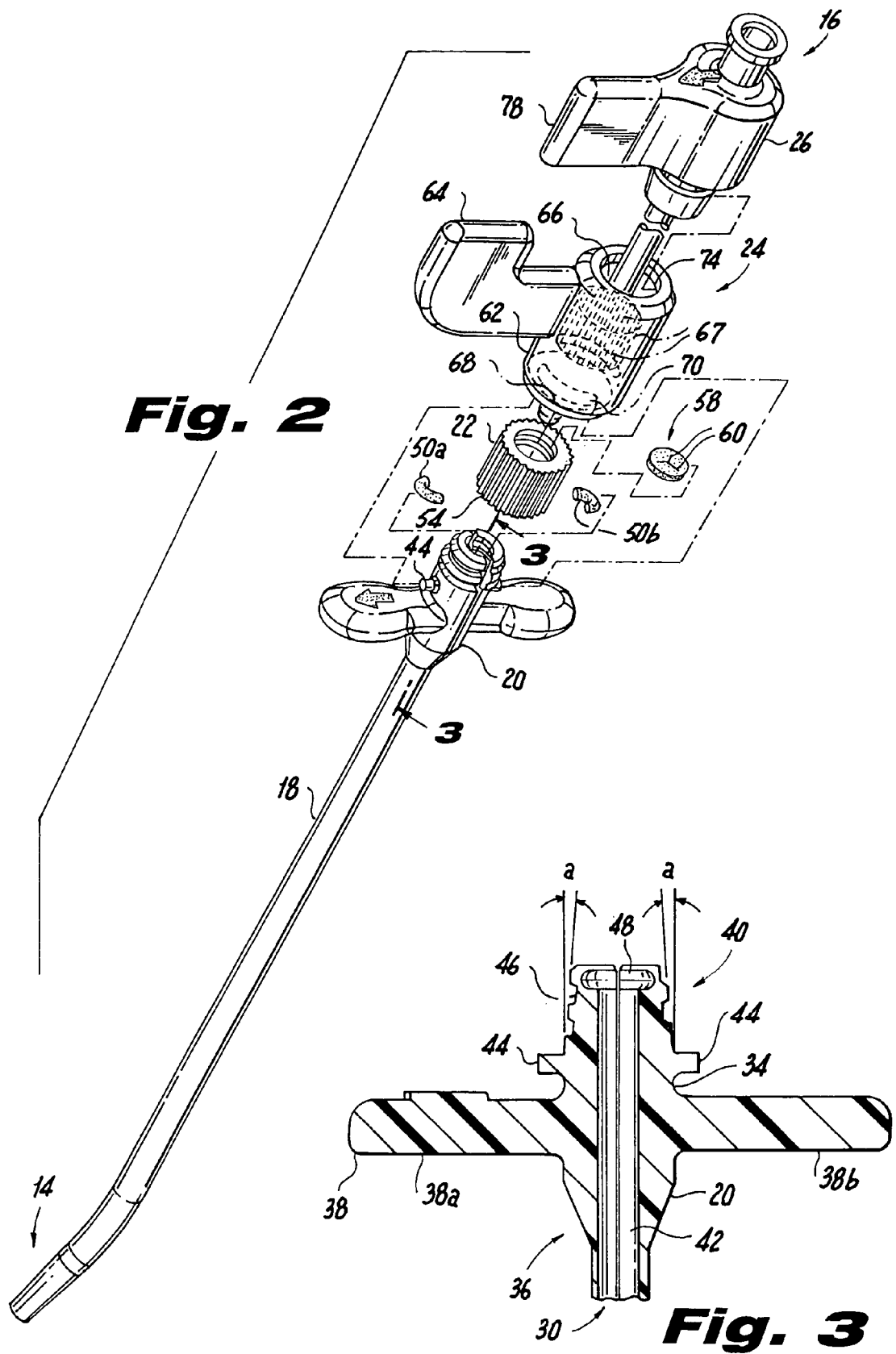

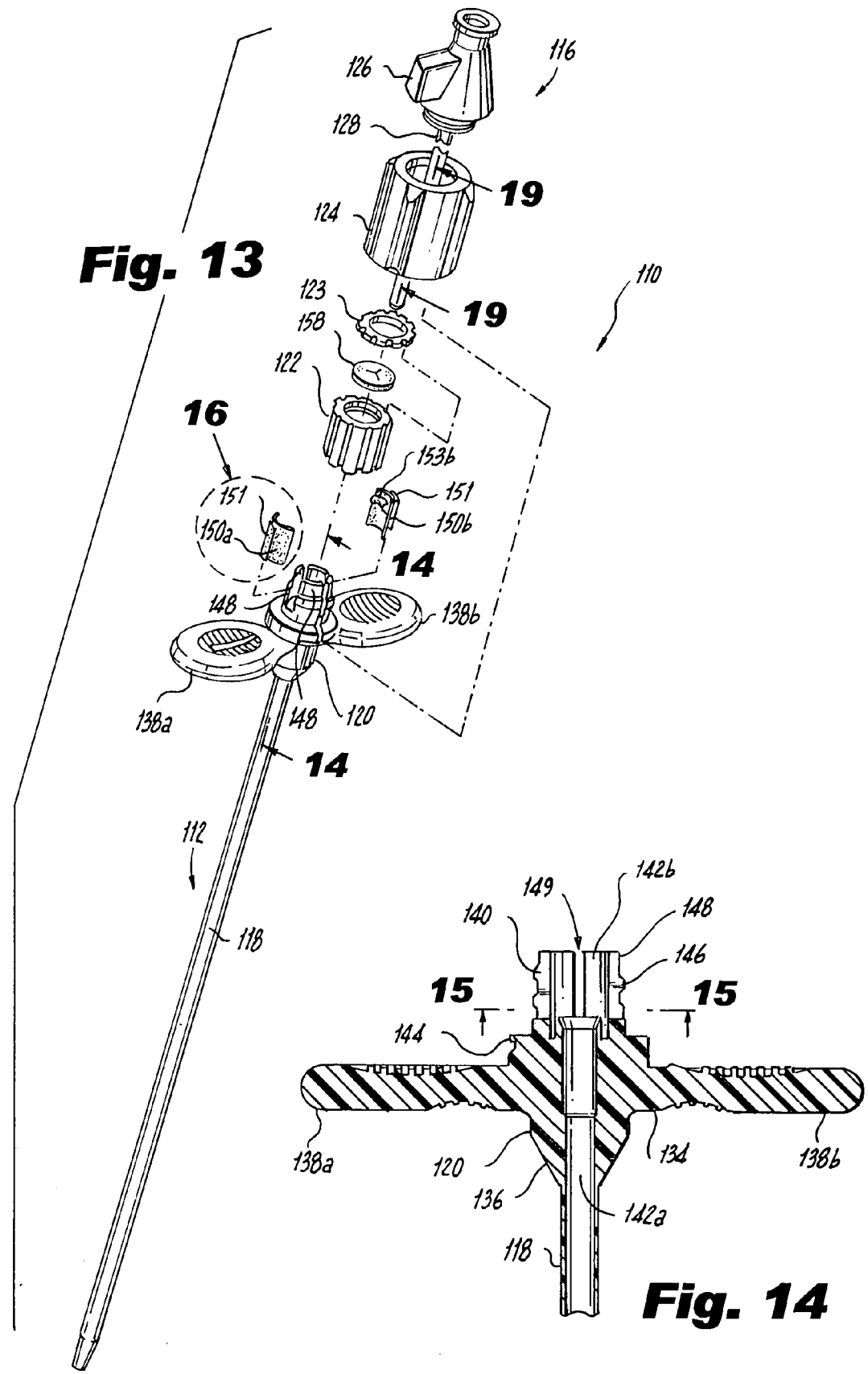

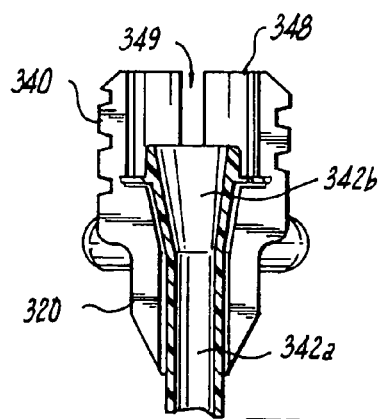
Fig. 29
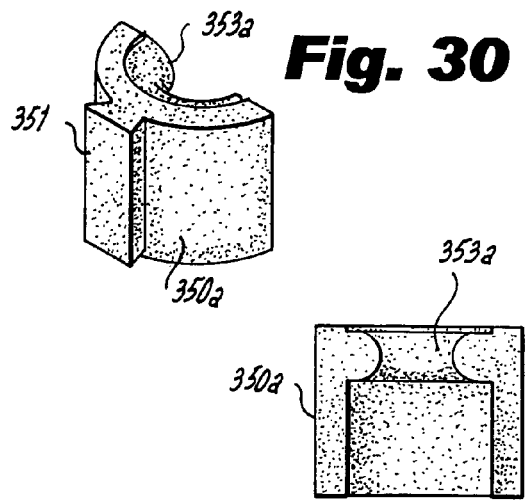
Fig. 30
Fig. 31
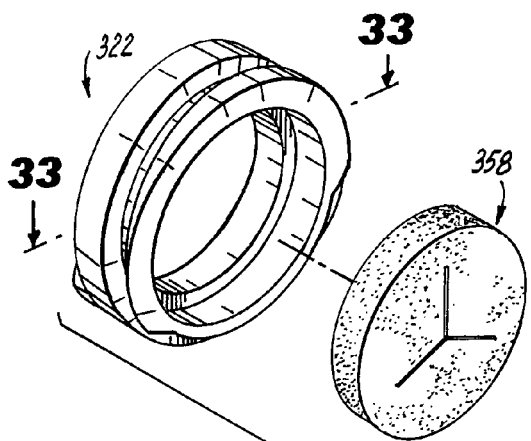
Fig. 32
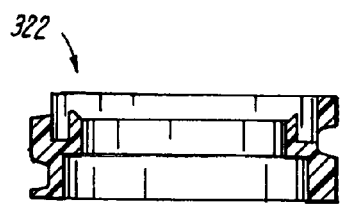
Fig. 33
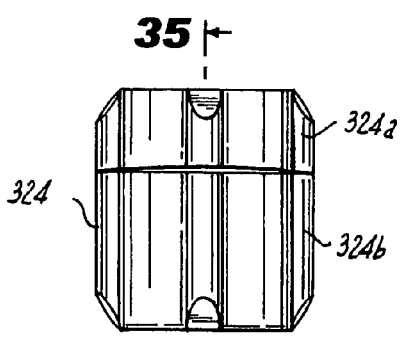
Fig. 34
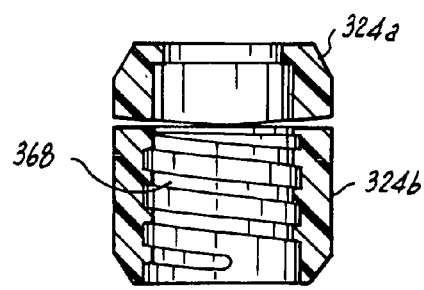
Fig. 35

LOCKING VASCULAR INTRODUCER ASSEMBLY WITH ADJUSTABLE HEMOSTATIC SEAL

CROSS-REFERENCE TO RELATED APPLICATION(S)

The subject application is a continuation in part of U.S. patent application Ser. No. 10/389,229 filed Mar. 14, 2003, now U.S. Pat. No. 7,192,433 which claims the benefit of priority to U.S. Provisional Patent Application No. 60/364,649 filed Mar. 15, 2002, and U.S. Provisional Patent Application No. 60/391,793 filed Jun. 27, 2002, the disclosures of which are herein incorporated by reference in their entireties.

BACKGROUND OF THE INVENTION

1. Field of the Invention

The subject disclosure relates to a vascular introducer assembly, and more particularly, to a vascular introducer assembly that includes a dilator, a sheath for accommodating the dilator, a locking mechanism for temporarily securing the dilator and the sheath to one another and an adjustable hemostatic seal for limiting fluid egress from the introducer assembly.

2. Background of the Related Art

The percutaneous introduction of diagnostic and/or therapeutic devices such as pacemaker leads and cardiovascular catheters into a blood vessel is typically accomplished with the aid of an introducer assembly. Introducer assemblies generally include a dilator having a tapered end portion and a thin-walled introducer sheath having a lumen extending therethrough to initially accommodate the dilator, and subsequently accommodate the passage of a pacemaker lead or catheter therethrough. Typically, the percutaneous introduction of an introducer assembly is accomplished by first inserting a needle into the blood vessel at a desired location and its position is verified by observing fluid return or by a similar method. While the needle is held firmly in place, a guidewire is inserted through the needle cannula to the desired depth. The guidewire is then held in place and the needle is withdrawn. Pressure is applied on the puncture site in order to minimize blood loss. Next, the introducer assembly is threaded over the guide wire. The introducer assembly is grasped close to the skin surface and advanced through the tissue to the desired position. Then, the dilator and guidewire are removed, leaving the sheath installed. A lead, catheter or similar diagnostic or therapeutic device is then introduced into the sheath and advanced to the desired position. Lastly, the sheath is removed, leaving the device disposed within the blood vessel of the patient.

It is known to configure an introducer sheath in such a manner so that it may be easily removed or separated from the lead or catheter after it has been emplaced. For example, it is known to provide score lines in the wall of the sheath to enable the sheath to be pealed away, slit or split open. Once the sheath is removed and catheter is emplaced, therapeutic medical devices such as endocardial pacing/defibrillation leads may he introduced into the blood vessel through the catheter.

Occasionally, the dilator slides out of the sheath during the insertion of the introducer assembly into a blood vessel. This significantly complicates the insertion procedure because the introducer assembly may not slide smoothly into the blood vessel and the insertion may not be effective. In some instances, when the dilator slides out of the sheath during insertion, the sheath may proceed completely through the vein, and break, bend, or tear. Also, if the dilator separates from the central lumen of the sheath, blood may flow undesirably from the vessel through the sheath.

In addition, once the sheath is inserted into a blood vessel, it provides a passage for the free flow of blood. This may result in significant blood loss to the patient. The sheath also provides an open passage for the introduction of air into the vein. This could cause an embolism in the venous system of the patient. To overcome these problems, vascular introducers have been developed with hemostatic valves that prevent the free flow of blood through the introducer sheath.

Examples of such prior art devices are disclosed in U.S. Pat. No. 5,124,904 to Lee and U.S. Pat. No. 5,409,463 to Thomas et al., the disclosures of which are incorporated herein by reference in their entireties. In each of these devices, the hemostatic valve is configured in such a manner so that it creates frictional resistance to the passage of therapeutic devices such as flexible cardiac leads. This makes introduction of the lead difficult and can actually cause damage to the lead.

It would be beneficial therefore, to provide a vascular introducer having a sheath with a hemostatic seal that may be selectively, radially adjusted to accommodate frictionless, unobstructed passage of a diagnostic or therapeutic device therethrough.

Furthermore, there is a need for a vascular introducer assembly that provides a mechanism for securely locking the dilator and sheath together during insertion of the introducer assembly to prevent axial movement of the dilator relative to the sheath.

SUMMARY OF THE INVENTION

The present invention provides a vascular introducer which overcomes the problems associated with the prior art.

In particular, the present invention is directed to a vascular introducer which includes an elongated dilator having a tapered distal end portion; an elongated hollow sheath having opposed proximal and distal end portions and an axial lumen extending therethrough to accommodate the dilator; and a selectively adjustable annular seal operatively associated with the proximal end portion of the sheath and configured for movement of the axial lumen between an open position in which the passage of instruments through the axial lumen is unrestricted and a closed position in which insertion of an instrument through the axial lumen is restricted.

The vascular introducer of the present invention may also include a hub which is operatively associated with the proximal end portion of the sheath. This hub has a body portion including an axial passage to accommodate the dilator therein and for being in fluid communication with the axial lumen, a distal end portion and a proximal end portion.

The vascular introducer of the present invention may further include a dilator handle and a locking collar. The dilator handle is configured for directing movement of the dilator relative to the sheath and has a body portion with a proximal portion including a receiving port in communication with the dilator and a distal portion including a tapered stem. The locking collar includes an axial bore therethrough, a proximal portion including an first seating engagement configured for rotatably mounting the tapered stem of the dilator handle therein and a distal portion including a second selectively lockable engagement configured for alternately securing and unsecuring the locking collar with the proximal end portion of the sheath. By securing the locking collar with the sheath, axial movement of the dilator relative to the sheath is restricted.

Preferably, the second selectively lockable engagement on the distal portion of the locking collar includes cooperative interlocking structures defined on the proximal end portion of the sheath and on an inner wall of the locking collar. These cooperative interlocking structures are engaged and disengaged by rotational movement of the locking collar relative to the proximal end portion of the sheath. Furthermore, it is preferable that the movement of the selectively adjustable annular seal between the open position and closed position is actuated by the engagement and disengagment of the locking collar with the proximal end portion of the sheath.

The present invention is also directed to a vascular introducer having an adjustable hemostatic seal. This embodiment of the present invention includes an elongate hollow sheath defining an axial lumen which has opposed proximal and distal end portions; a hub operatively associated with the proximal end portion of the sheath which includes a hub body portion with an axial bore in fluid communication with the axial lumen of the sheath, and a tapered proximal portion having a helical thread defined along an outer periphery thereof and a recessed channel defined circumferentially along an inner periphery thereof; an elastic annular seal disposed within the recessed channel of the hub; and a cap having an axial bore extending therethrough with a helical thread for cooperating with the helical thread of the tapered proximal portion of the hub so that rotational movement of the cap relative to the hub causes the annular seal to move radially relative to the axial bore of the hub.

This embodiment of a vascular introducer constructed in accordance with the present invention may be configured so that the radial movement of the annular seal, which may be fabricated of an elastomeric material such as silicone, is actuated by axial rotation of the cap about a 90 degree arc. Preferably, the aforementioned vascular introducer of the present invention also includes handle members protruding radially from the hub body portion.

In a preferred embodiment of the vascular introducer of the present invention, a trocar seal is disposed about the axial bore of the cap to prevent fluid flow from the lumen and permit insertion of devices through the axial bore of the cap.

The present invention is also directed to a vascular introducer which includes an elongated dilator having a tapered distal end portion and an axial passage extending therethrough; an elongated hollow sheath having opposed proximal and distal end portions and an axial lumen extending therethrough to accommodate the dilator; a hub operatively associated with the proximal end portion of the sheath which includes a hub body portion with an axial passage for accommodating the dilator and being in fluid communication with the axial lumen of the sheath, and a tapered proximal portion; a dilator handle associated with a proximal end of the dilator including a proximal receiving port in communication with the axial passage of the dilator and a distal mounting stem; and a locking collar having an axial bore with a proximal portion configured to receive the distal mounting stem of the dilator handle to facilitate rotation of the dilator handle and a distal portion configured to engage the tapered proximal portion of the hub.

The aforementioned embodiment of a vascular introducer constructed in accordance with the present invention can include cooperative interlocking structures defined on the distal portion of the locking collar and the tapered proximal portion of the hub. Preferably, these cooperative interlocking structures are configured to be engaged by rotational movement of the locking collar relative to the hub about a 90 degree arc through an axial plane. In one embodiment, the cooperative interlocking structures include a pair of pins radially projecting from the tapered proximal portion of the hub and a corresponding pair of receiving slots for the pins defined in an interior wall of the locking collar.

The aforementioned vascular introducer may also include the selectively adjustable annular seal operatively associated with the proximal end portion of the hub and configured for movement of the axial passage between an open position in which the passage of instruments through the axial lumen is unrestricted and a closed position in which insertion of an instrument through the axial lumen is restricted as described above.

Preferably, the vascular introducer is configured such that the engagement of the distal portion of the locking collar with the tapered proximal portion of the hub moves the axial passage to the closed position. Even more preferably, the adjustable seat and the cooperative interlocking structures are alternatively engaged and disengaged by rotational movement of the locking collar about a 90 degree arc in the axial plane.

In one embodiment of the present invention, the selectively adjustable annular seal includes a threaded portion defined on the tapered proximal portion of the hub; a circumferential recessed channel defined in an interior wall of the tapered proximal portion of the hub; an annular compressible sealing ring disposed in the circumferential recessed channel of the hub, and a sealing cap having an axial bore and a threaded portion defined therein for being threadably engaged with the threaded portion defined on the tapered proximal portion of the hub, wherein the annular compressible sealing ring in the circumferential recessed channel of the tapered proximal portion of the huh is selectively moved from a compressed position in which fluid egress through the axial passage is restricted and a decompressed position in which fluid egress through the axial passage is unrestricted by alternate threadable engagement of the sealing cap. Preferably, the sealing cap is seated within the axial bore of the locking collar such that alternate rotational movement of the locking collar effectuates the threaded engagement and disengagement of the sealing cap with the tapered proximal portion of the hub.

The present invention is also directed to a vascular introducer which includes an elongated splitable sheath having opposed proximal and distal end portions, and an axial lumen extending therethrough to accommodate a dilator. A handle portion operatively associated the proximal end portion of the sheath includes a splitable central hub and an axial bore therein forming a passageway into the central lumen of the sheath. A pliable seal is disposed within a proximal portion of the splitable central hub. Preferably the pliable seal is a two-part annular seal, and more preferably, the seal is a two-part cylindrical seal.

There is an actuator configured for mounting on the splitable central hub between a first position and a second position for, among other things, controlling the hemostatic valve. The actuator can be mounted in the first position, which results in a decrease in diameter of the axial bore in the central hub relative to the diameter of the axial bore when the actuator is mounted in the second position.

The actuator can also be made splitable. One embodiment of a splitable actuator disclosed herein includes two generally symmetrical arcuate members having corresponding male and female interlocking features for facilitating engagement to one another.

Preferably, the actuator and proximal end portion of the hub contain threaded portions which permit the actuator to be mounted on the proximal end portion, although other configurations for facilitating the engagement of these components are within the scope of the present invention. In this embodiment, the actuator is placed in the first position upon being fully threaded onto the proximal end portion, and conversely, is in the second position upon being de-threaded (without being removed from the proximal end portion). It is also preferable that the proximal end portion of the central hub consist of axial tabs which on their exterior surfaces form threads and are resilient yet sufficiently pliable to move inward radially upon the application of pressure by the actuator in the mounted position.

The actuator can also consist of a proximal portion operatively associated with the dilator and a distal portion configured for mounting on the proximal portion of the splitable central hub, wherein the proximal and distal portions of the actuator are configured to be separable relative to one another.

In another embodiment, a vascular introducer constructed in accordance with the present invention includes an annular member having an axial bore and trocar seal disposed therein. The annular member is configured for mounting on the proximal end portion of the splitable central hub and facilitates the mounting of the actuator in the first position, among other things.

In another embodiment, the present invention is directed to a vascular introducer that includes an elongated dilator having a tapered distal end portion, an elongated splitable sheath having opposed proximal and distal end portions and having an axial lumen extending therethrough to accommodate the dilator, a handle portion operatively associated the proximal end portion of the sheath and including a splitable central hub having an axial bore defined therein forming a passageway into the axial lumen, a two-part annular seal disposed within the proximal portion of the splitable central hub of the handle portion, and an actuator configured for mounting on the proximal portion of the splitable central hub between a first position and a second position, wherein the actuator mounted in the first position causes the two-part annular seal to move radially inward relative to the position of the two-part annular seal when the actuator is mounted in the second position.

The present invention is also directed to a vascular introducer that includes an elongated sheath having opposed proximal and distal end portions and having an axial lumen extending therethrough, a handle portion operatively associated the proximal end portion of the sheath and including a central hub having an axial bore defining a passageway into the axial lumen of the sheath, a cylindrical seal disposed within the proximal end portion of the central hub of the handle portion, and an actuator configured for mounting on the central hub between a first position and a second position. Changing the position of the actuator from the first position to the second position decreases the diameter of the axial bore in the splitable central hub relative to the diameter of the axial bore when the actuator is mounted in the second position.

The cylindrical seal can include a radially inner projecting ring and be divided into two substantially symmetrical parts. The proximal end portion of the central hub can also include an engagement for securing the cylindrical seal therein. In this embodiment, the handle portion, central hub and sheath can be made splitable.

Also, although the trocar seal is preferred, a seal member other than a trocar seal having three slits, such as a seal member having one or more slits, can be used instead in any of these embodiments of the present invention.

Further features of the vascular introducer of the subject invention will become more apparent from the detailed description of the present invention that follows taken in conjunction with the drawings.

BRIEF DESCRIPTION OF THE DRAWINGS

So that those having ordinary skill in the art to which the present application appertains will more readily understand how to make and use the same, reference may be had to the drawings wherein:

FIG. 2 is an exploded perspective view of the vascular introducer assembly of FIG. 1 with parts separated for ease of illustration;

FIG. 3 is an enlarged cross sectional view of the hub portion of the vascular introducer assembly of FIG. 1;

FIG. 13 is an exploded perspective view of a vascular introducer assembly constructed in accordance with another preferred embodiment of the subject invention with parts separated for ease of illustration;

FIG. 14 is an enlarged cross sectional view of the hub portion of the vascular introducer assembly of FIG. 13;

FIG. 29 is an enlarged cross sectional view of the proximal end portion of the hub portion of the vascular introducer of FIG. 27, taken along the line 29-29 in FIG. 28, illustrating the threaded axial tab configuration, funnel entrance to the axial bore through the hub portion, and axial bores of differing diameter, among other things;

FIG. 30 is a perspective view of one part of the two-part sealing ring constructed in accordance with the present invention for use with the vascular introducer of FIG. 27, illustrating the arcuate shape, radially inward annular ring portion and outer notch for engaging the threaded axial tab on the proximal end portion of the hub portion of the vascular assembly shown in FIG. 27;

FIG. 31 is a front view of the part of the sealing ring shown in FIG. 30;

FIG. 32 is an exploded perspective view of the annular member constructed in accordance with the present invention for use with the vascular introducer of FIG. 27, illustrating the threaded exterior and trocar seal, among other things;

FIG. 33 is a cross sectional view of the annular member of FIG. 32, taken along line 33-33 in FIG. 32, illustrating the threading, among other things;

FIG. 34 is a front view of the locking collar constructed in accordance with the present invention, illustrating the location in which the locking collar can be separated into two parts;

FIG. 35 is a cross sectional view of the locking collar of FIG. 34, taken along line 35-35 in FIG. 34, illustrating the locking collar configuration including two separable portions, the first having an interior threading and the other being non-threaded, among other things;

These and other features of the vascular introducer assembly of the subject invention will become more readily apparent to those having ordinary skill in the art from the following description of the preferred embodiment.

DETAILED DESCRIPTION OF THE INVENTION

In the following detailed description of the present invention, references are made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. The following detailed description is, therefore not to be taken in a limiting sense, and the scope of the present invention is defined by the appended claims and equivalents thereof.

Figure 1:
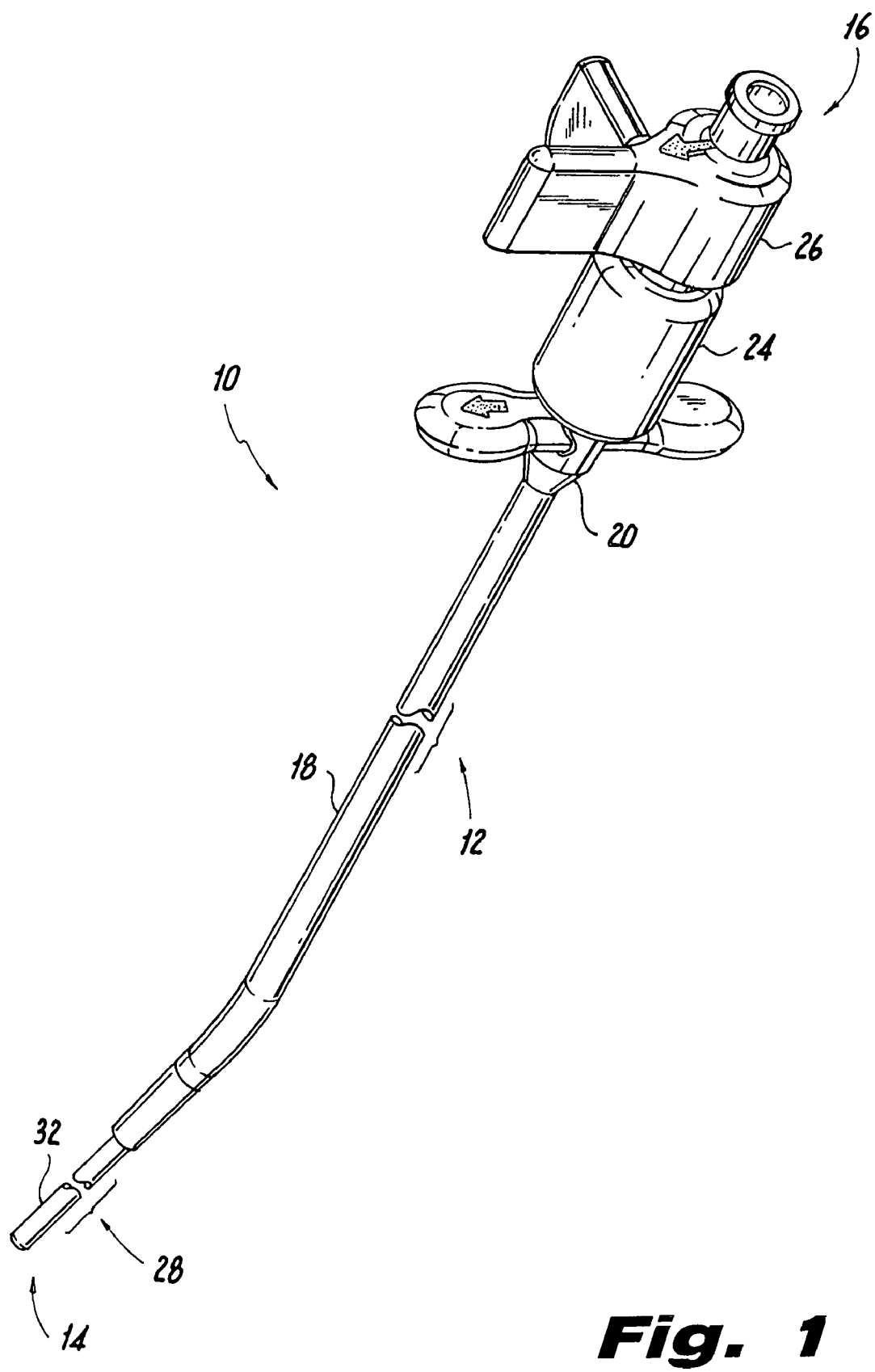
FIG. 1 is a perspective view of a vascular introducer assembly constructed in accordance with a preferred embodiment of the subject invention in a fully assembled condition.

Referring now to the drawings wherein like reference numerals identify similar structural features of the invention, there is illustrated in FIG. 1, a vascular introducer assembly constructed in accordance with a preferred embodiment of the subject invention and designated generally by reference numeral 10. Vascular introducer assembly 10 generally includes an elongated tubular body 12. The general shape and orientation of assembly 10 as shown in FIG. 1 defines a longitudinal axis and an axially opposed distal end 14 and proximal end 16 relative thereto, and these designations will be used as a convention throughout the following description to describe the components and features of the present invention.

Referring now to both FIGS. 1 and 2, this embodiment of introducer assembly 10 has a body 12 that generally includes (listed in order from distal end 14 to proximal end 16) an outer sheath 18, an engagement hub 20, a sealing cap 22, a locking collar 24 and a dilator handle 26, each of which are disposed over a hollow elongate dilator 28 and will be discussed in further detail herein below.

Figure 4:
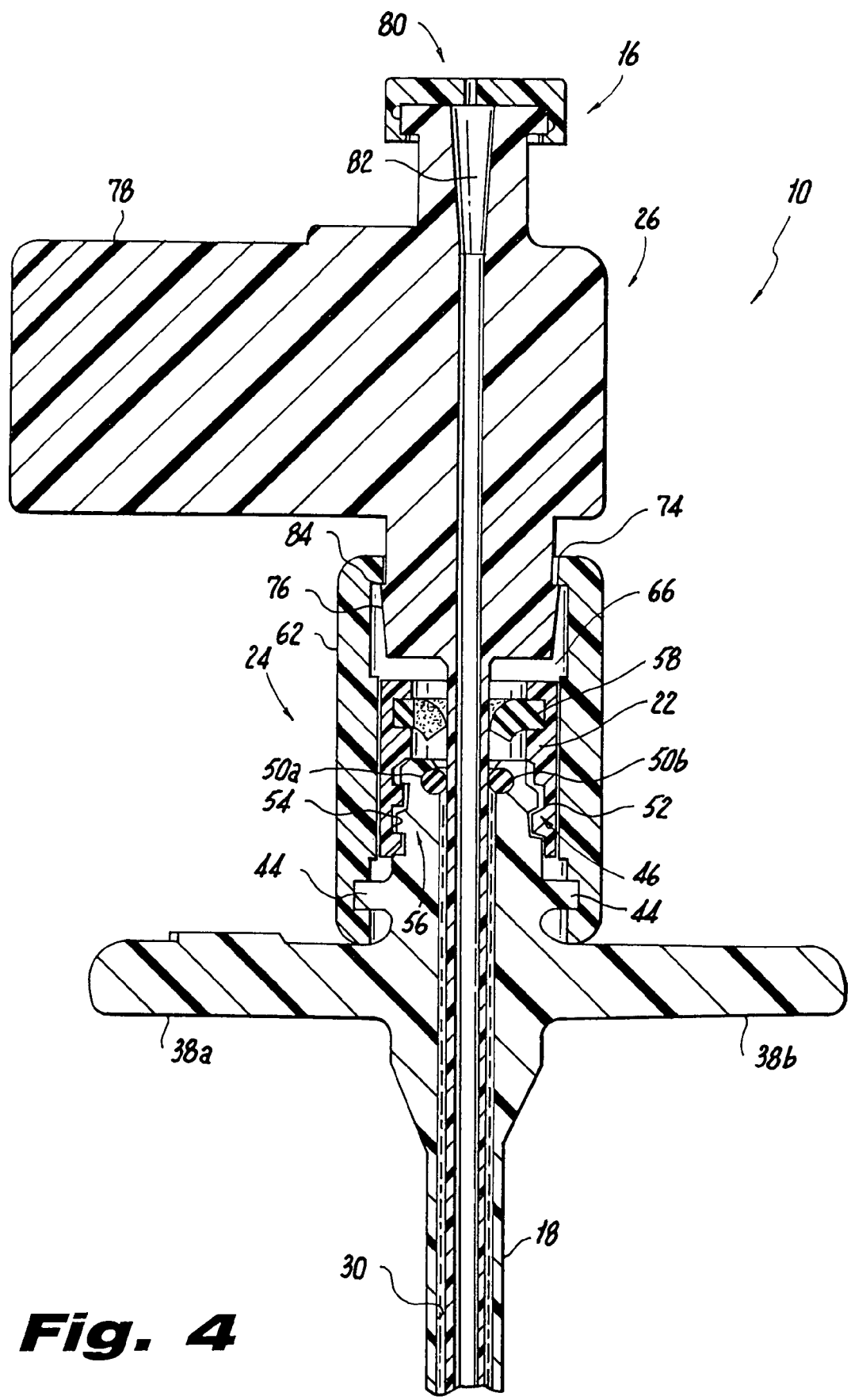
FIG. 4 is an enlarged cross sectional view of the proximal portion of the vascular introducer assembly of FIG. 1 with the rotatable locking collar in a locked position to prevent axial movement of the dilator relative to the sheath and the hemostatic seal in a closed position which restricts access through the axial lumen of the sheath.

Beginning with the distal-most component of assembly 10, outer sheath 18 is hollow and elongate. As shown in FIGS. 3 and 4, outer sheath 18 defines an interior axial lumen 30 for, among other things, accommodating dilator 28. As illustrated in this embodiment, dilator 28 includes a curved distal end portion 32, which, among other things, facilitates endocardial lead placement into areas of the heart that are difficult to access by intravascular means, such as the coronary sinus, but may also be straight or shaped in some other manner as well. Sheath 18 is preferably constructed of a compliant and flexible but resilient material that permits it to assume a curved form corresponding to the curvature of distal end portion 32. Preferably, sheath 18 is fabricated so that its shape may vary depending upon the intended use of the introducer.

Referring now to FIG. 3, along with continuing reference to FIGS. 1 and 2, engagement hub 20 generally includes a central body portion 34 having a tapered distal end portion 36, a sheath handle 38, a tapered proximal end portion 40 and an axial bore 42 therethrough in fluid communication with axial lumen 30. Tapered proximal end portion is sloped inwardly at an angle a, which is preferably between about 1 and about 8 degrees relative to the longitudinal axis defined by introducer 10. In this embodiment, sheath handle 38 includes a pair of opposing, radially outward projecting portions 38a and 38b. Preferably, the axial bore 42 is substantially aligned with and about the same diameter as axial lumen 30.

Proximal end portion 40 is fabricated of a flexible yet resilient material and includes a pair of opposed, radially outward projecting pins 44 positioned distally relative to a threaded portion 46 defined on the exterior of the proximal end portion 40, which is tapered as mentioned above so that its outer diameter generally decreases axially in the proximal direction. A circumferential channel 48 for receiving an annular sealing ring 50 therein is defined along the interior wall of proximal end portion 40 adjacent to its proximal end. Preferably, annular sealing ring 50 is fabricated from a flexible yet resilient material such as silicone. In this embodiment, annular sealing ring 50 includes a pair of semi-circular portions 50a and 50b.

Sealing cap 22 includes a body 52 having axially defined, substantially parallel grooves or flutes defined on its exterior and an axial bore 54 with a threaded portion 56 configured to engage the threaded portion 46 defined on the exterior of proximal end portion 40 of hub 20. Preferably, and as shown with specificity in FIG. 2, cap 22 further includes a trocar seal 58 disposed over axial bore 54 at the proximal end of cap 22.

Trocar seal 58 generally consists of a flexible but resilient material having three slits 60 defined therein which extend radially outward from its center to form three flaps. The three flaps may be forcibly opened to receive the dilator or other device while impeding fluid egress from the sealing cap 22.

Locking collar 24 includes a central body 62 having a single, radially outward projecting L-shaped handle 64 an axial bore 66 for receiving scaling cap 22. In this embodiment, axial bore 66 includes axially defined, substantially parallel grooves or flutes 67 for interlocking with the exterior scaling cap 22 so that rotational movement of collar 24 (i.e., movement not in the axial direction) results in the rotational movement of sealing cap 22 in accordance therewith. Collar 24 also includes a pair of slots 68 that are recessed in the interior wall of body 62 which defines axial bore 66 adjacent to the distal end of collar 24. Slots 68 are configured and dimensioned to receive pins 44 of hub 20 and cooperate together to secure locking collar 24 with the proximal end portion 40 of hub 20.

Slots 68 each include an axial portion 70 which extends in the proximal direction along the interior of collar 24 and is joined with a circumferential portion 72 that extends circumferentially along the interior periphery of collar 24. Collar 24 further includes a circular rim 74 defined at the proximal end of central body 56.

Dilator handle 26 includes a tapered distal stem portion 76, a single, radially outward projecting handle 78, a proximal receiving port 80 and an axial bore 82 therein. Tapered distal stem portion 76 includes a ridge 84 for engaging the circular rim 74 at the proximal end of collar 24 so that dilator handle 26 is rotatably mounted in the proximal end of collar 24. Axial bore 82 is in fluid communication with dilator 28 and proximal receiving port 80, thus, objects or devices such as endocardial leads may be inserted into dilator 28 via proximal receiving port 80.

Figure 5:
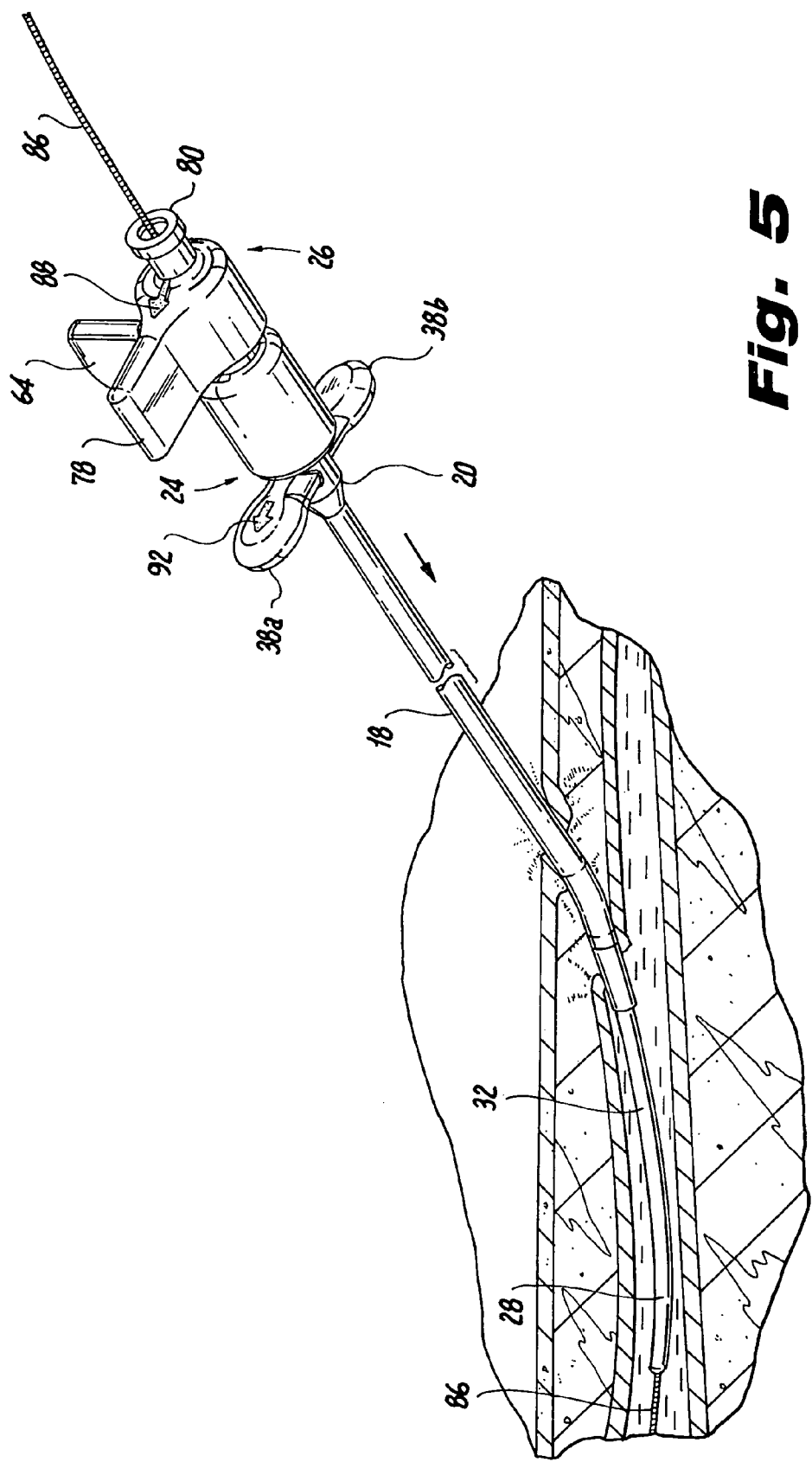
FIG. 5 is a perspective view of the vascular introducer assembly of FIG. 1 being percutaneously introduced into a blood vessel along a guidewire.

In use, the dilator 28 in vascular introducer assembly 10 is inserted over a guidewire 86, as shown in FIG. 5 and as described in the above background section. An arrow 88 is defined radially along the projecting handle 78 of dilator handle 26 to identify the relative direction of the curvature in distal end portion 32 of dilator 28. The locking collar 24, dilator handle 26 and sealing cap 22 cooperate to generally define a rotatable sheath lock and hemostatic seal. As Illustrated in FIG. 5, collar 24 is in the locked position on pins 44 (not shown in FIG. 5), which increases the rigidity and stability of the introducer assembly 10 for intravenous insertion, among other things.

As previously noted, rotational movement of collar 24 simultaneously causes the rotation of sealing cap 22, which is interlocked with collar 24 by flutes 67 in axial bore 66. As shown in FIG. 4, placing collar 24 in the locked position (i.e., pins 44 engaged within the circumferential portion 72 of slots 68) rotates sealing cap 22 in the clockwise direction on threaded portion 46 of the tapered proximal end portion 40 of hub 20. By twisting sealing cap 22 clockwise, cap 22 also moves distally with respect to proximal end portion 40, which causes a crimping action that forces proximal end portion 40 radially inward. This action reduces the diameter of axial bore 42 so that the annular sealing ring 50 at the proximal end of axial bore 42 closes around dilator 28, thus, impeding fluid (i.e., blood) flow entering via the distal end of lumen 30 from exiting through bore 42 and restricting insertion of devices into lumen 30.

Figure 6:
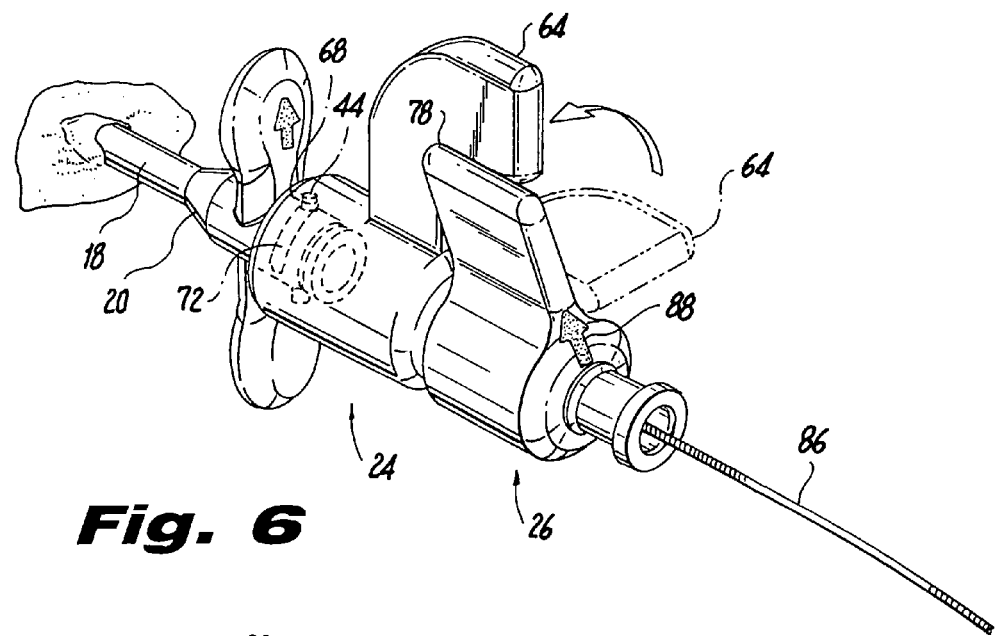
FIG. 6 is a perspective view of the proximal portion of the vascular introducer of FIG. 1 illustrating the rotational movement of the locking collar which moves the hemostatic seal to an open position in which passage of instruments through the axial lumen of the sheath is unrestricted.
Figure 7:
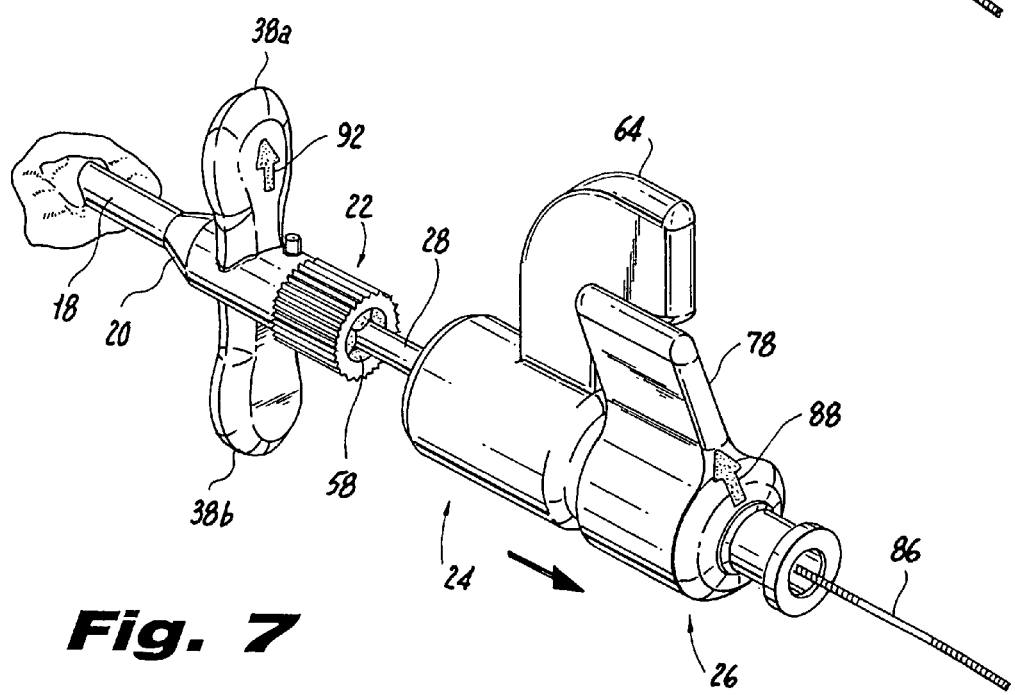
FIG. 7 is a perspective view of the vascular introducer of FIG. 1 illustrating the manner in which the rotatable locking collar and dilator are separated from the sheath and also showing the hemostastic seal which remains intact on the hub portion of the introducer.

Referring now to FIGS. 6 and 7, rotating collar 24 counterclockwise, so that outwardly projecting handle 64 of collar 26 is adjacent handle 78 on dilator handle 26, unlocks pins 44 from slots 68. Sealing cap 22 is also rotated counterclockwise which causes the movement of cap 22 along threaded portion 46 in the proximal direction which releases the aforementioned crimping action. Thus, fluid flow through axial bore 42 is no longer impeded by sealing ring 50. Preferably, the circumferential portions 72 of slots 68 in collar 24 are sufficiently elongated so that collar 24 can be fastened onto pins 44, or unfastened therefrom, by rotating the collar 24 about 90 degrees in either direction.

As shown in FIG. 7, rotating collar 24 to unlock collar 24 from pins 44 in hub 20 allows the collar, along with dilator handle 26 and dilator 28, to move axially and be disengaged from the remaining components (i.e., sealing cap 22, hub 20 and outer sheath 18) in this embodiment of introducer assembly 10.

Figure 8:
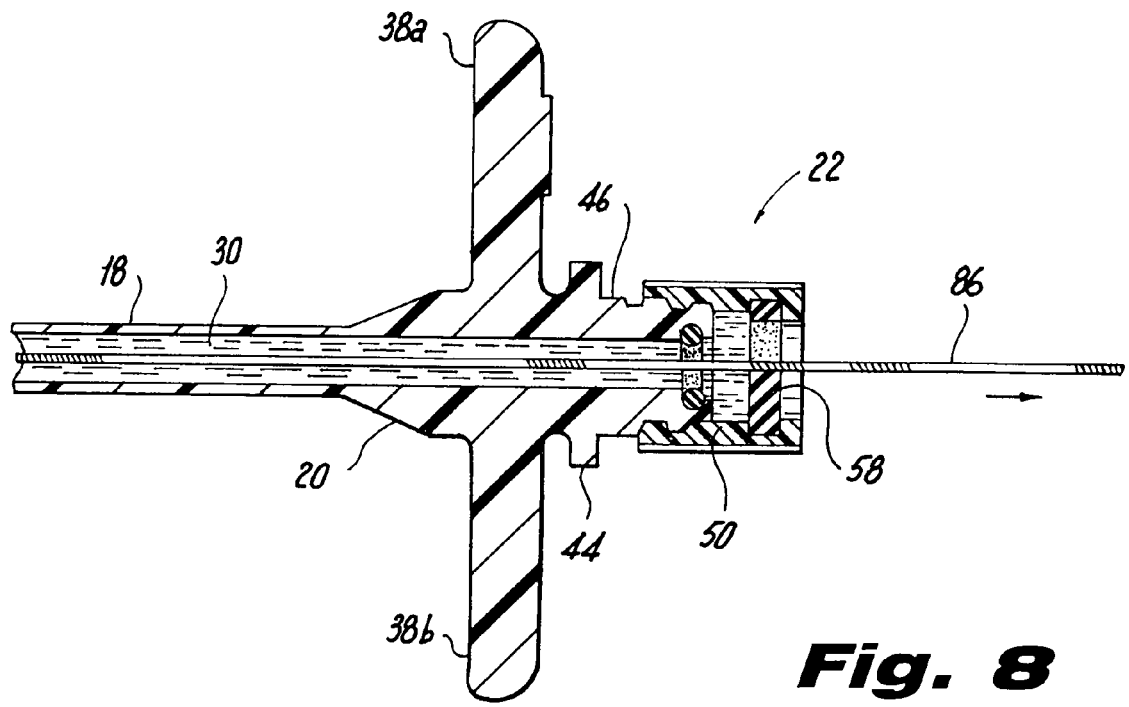
FIG. 8 is a cross sectional view of the hub portion and sealing cap of the vascular introducer assembly of FIG. 1 after the rotatable locking collar and dilator have been removed therefrom to illustrate the components of the present invention forming the adjustable hemostatic seal, with the seal being disposed in an open position in which passage of instruments through the axial lumen of the sheath is unrestricted.
Figure 9:
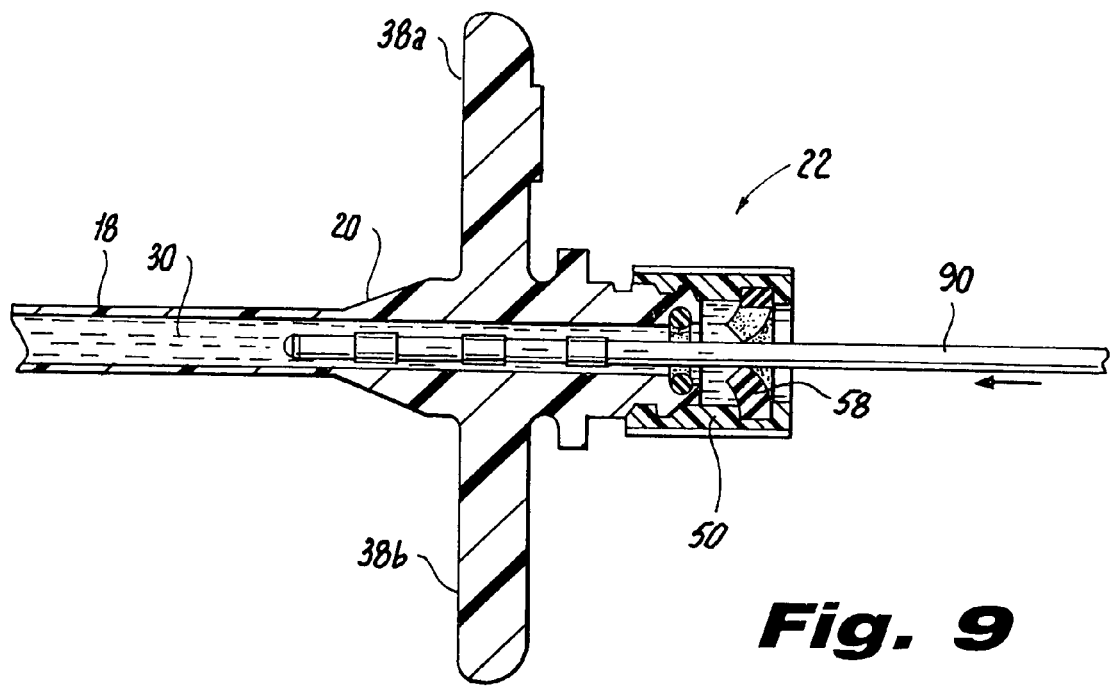
FIG. 9 is a cross sectional view of the hub portion and sealing cap as shown in FIG. 1, which illustrates the valve in an open position with an endocardial lead being inserted through the trocar seal of the sealing cap.
Figure 10:
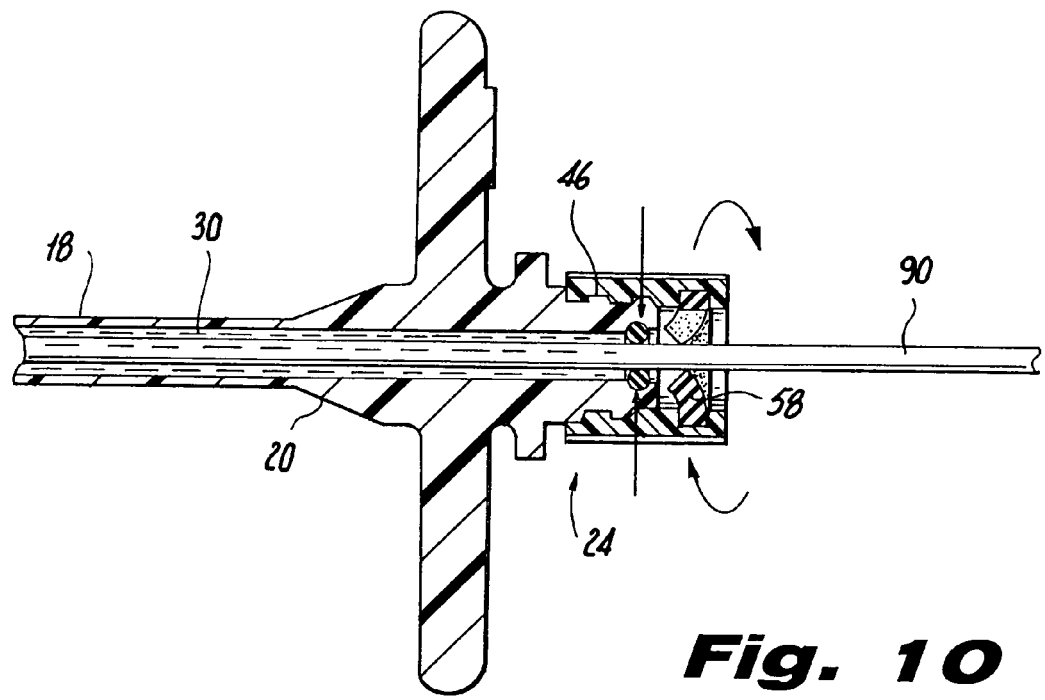
FIG. 10 is a cross sectional view of the hub portion and sealing cap shown in FIG. 9, along with the dilator disposed in the lumen of the introducer assembly, illustrating the movement of the sealing cap relative to the hub so that the hemostatic seal radially compresses around the dilator.

As shown in FIGS. 8 and 9, trocar seal 58 inhibits fluid flow entering lumen 30 from exiting cap 22 when collar 24, dilator handle 26 and dilator 28 are removed from introducer assembly 10. This allows guidewire 86 to he removed so that introducer assembly 10 may be used to insert devices or equipment, such as an endocardial lead 90, intravenously through lumen 30. In addition, dilator 28 and other associated components may be reinserted through lumen 30, and cap 22 may be threaded onto threaded portion 46 thereafter so that the aforementioned crimping action is applied, as shown in FIG. 10.

Figure 11:
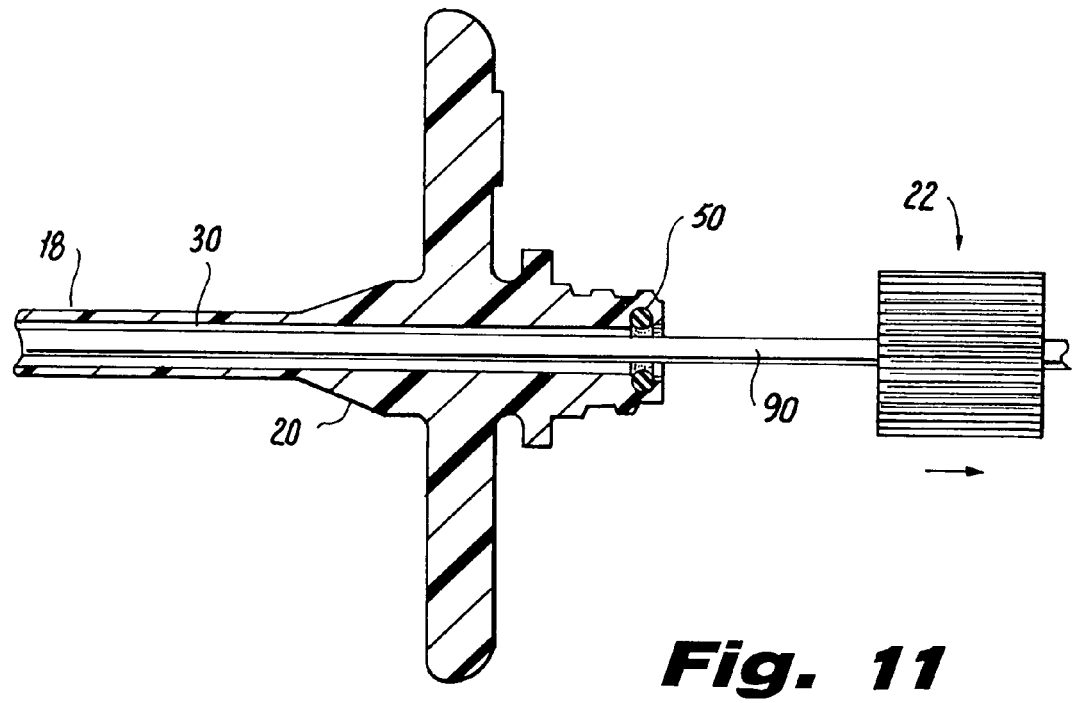
FIG. 11 is a cross sectional view of the hub portion of FIG. 10 illustrating the manner in which the sealing cap is removed from the hub when the hemostatic seal is in an open position.
Figure 12:
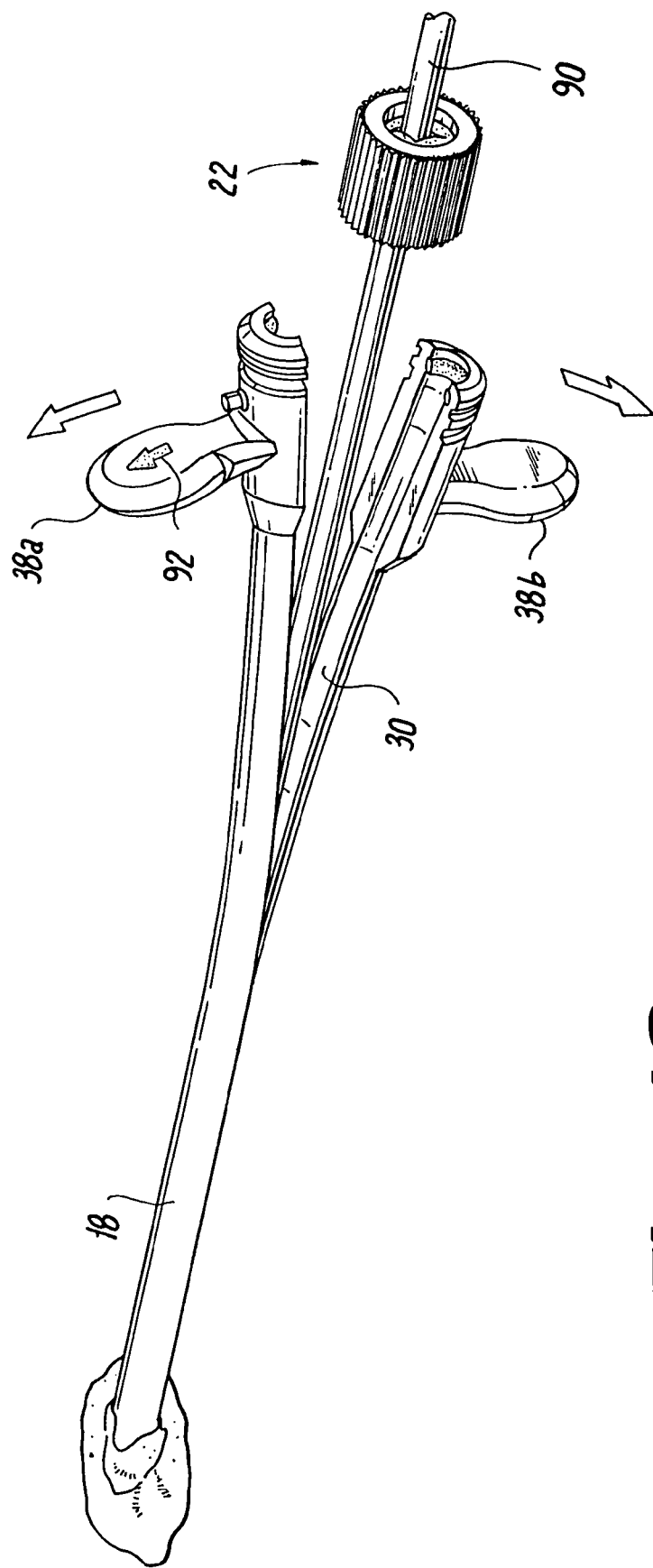
FIG. 12 is a perspective view of the vascular assembly of the subject invention illustrating the manner in which the sheath is split along score lines to facilitate removal from the operative site.
Figure 15:
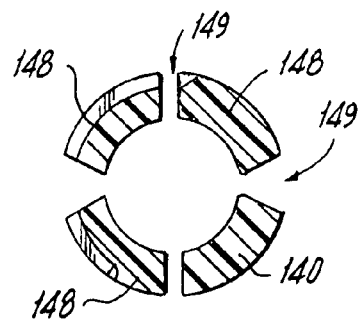
FIG. 15 is an enlarged cross sectional view of the proximal end portion of the hub portion of the vascular introducer of FIG. 13, taken along the line 15-15 in FIG. 14, illustrating the threaded axial tab configuration.
Figure 16:
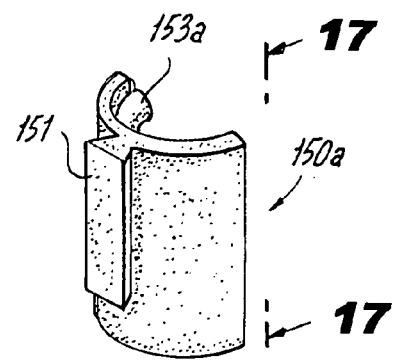
FIG. 16 is a perspective view of one part of the two-part sealing ring constructed in accordance with the present invention for use with the vascular introducer of FIG. 13, illustrating the arcuate shape, radially inward annular ring portion and outer notch for engaging the threaded axial tab on the proximal end portion of the hub portion of the vascular assembly shown in FIG. 13.

As illustrated in FIG. 11, cap 22 may be threaded off and removed from hub 20. As described in the background section, this is essentially the first step in the removal of the introducer assembly 10, and facilitates removal of outer sheath 18 and hub 20. As shown in FIG. 12, in this embodiment, outer sheath 18 and hub 20 can be split substantially in half by pulling both handles 38a and 38b of hub 20 apart in opposing radial directions. Handle 38a is marked with an arrow 92 pointing in the radial direction as a guide. Preferably, outer sheath 18 and hub 20 are constructed with axially opposing weakened zones or score lines that facilitate dividing sheath 18 as shown in FIG. 12, without compromising the integrity of sheath 18 or restricting use of sheath 18 for any of its intended purposes.

FIGS. 13-24 disclose another embodiment of a vascular introducer assembly constructed in accordance with the present invention which is designated generally by the reference numeral 110. Body 112 of introducer assembly 110 includes (from distal end 114 to proximal end 116) an outer sheath 118, an engagement hub 120, a fluted sealing cap 122, a locking collar 124 and a dilator handle 126, which are all configured and dimensioned for being disposed over a dilator 128.

In this embodiment, the proximal end portion 140 of hub 120 includes a proximal threaded portion 146 which corresponds with and is configured to engage threaded portion 156 defined within sealing cap 122. A distal threaded portion 144 is also defined on the proximal end portion 140 of hub 120 that is configured to engage threads 168 defined on the distal portion of the interior of locking collar 124 for securing locking collar 124 to hub 120. As in previous embodiments, locking collar 124 is connected at the proximal end with dilator handle 126 in a manner which permits rotational movement of dilator 128.

Also in this embodiment, axial bore 142 of hub 120 includes a distal end portion 142a having a first diameter, which extends through the majority of hub 120, and a proximal end portion 142b having a second diameter, which extends primarily through proximal end portion 140. The second diameter of proximal end portion 142b is configured and dimensioned to be of sufficient size to receive devices for intravenous insertion without jeopardizing the effectiveness of seal 150 in forming a fluid tight seal with dilator 128 when actuated to do so by sealing cap 122. In this embodiment, the second diameter in bore 142b is larger than the first diameter of bore 142a.

Proximal end portion 140 also includes four independent axial tabs 148 that define four axial slots 149. Axial tabs 148 each include a partial threading thereon which taken together form threaded portion 146 for receiving sealing cap 122. As can be best viewed in FIG. 15, two of the four axial slots 149 are keyed or otherwise shaped for receiving a triangular notch 151 on cylindrical sealing tube 150 with a radially inward projecting ring 153. Sealing tube 150 is divided into two symmetrical semi-cylindrical or "half-pipe" sections 150a and 150b, each including a substantially half portion of radially inward projecting ring 153, referred to as half-rings 153a and 153b, respectively.

Figure 17:
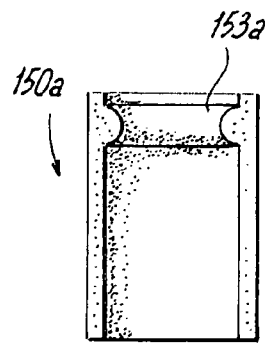
FIG. 17 is a front view of the part of the sealing ring shown in FIG. 16, taken along line 17-17 in FIG. 16.
Figure 19:
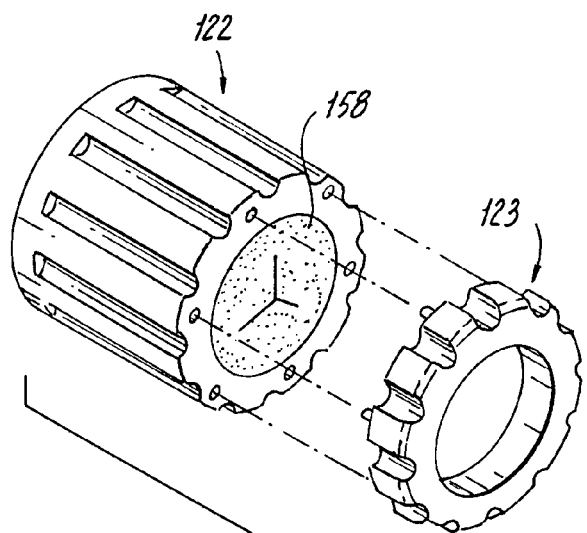
FIG. 19 is a cross sectional view of the locking collar constructed in accordance with the present invention for use with the vascular introducer of FIG. 13, taken along line 19-19 in FIG. 13, illustrating the threaded portion therein, among other things.

As can be best viewed in FIGS. 13 and 17, half-rings 153a and 153b are adjacent the proximal end of each half-pipe sections 150a and 150b and together generally form a circle of smaller diameter than the diameter of the circle formed by half-pipe sections 150a and 150b. The other two slots 149 in proximal end portion 140 that do not receive a triangular notch 151 facilitate a tight seal of the passageway by being sufficiently pliable to be moved radially inward to restrict axial bore 142b when a crimping action is applied to proximal end portion 140 by the distal threading of sealing cap 122.

Figure 18:
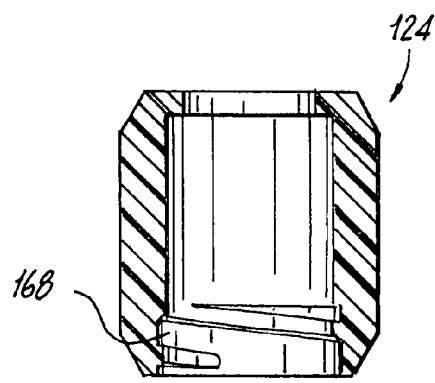
FIG. 18 is an exploded perspective view of the sealing cap member constructed in accordance with the present invention for use with the vascular introducer of FIG. 13, illustrating the trocar seal and removable proximal ring portion, among other things.

As shown best in FIG. 18, sealing cap 122 of this embodiment includes a removable annular rim 123 at its proximal end. Annular rim 123 is secured to cap 122 by dowels 125 which preferably snap-fit into holes 127. A trocar seal 158 is disposed over axial bore 154 through sealing cap 122, and is secured in part by the engagement of annular rim 123 with cap 122. Threads 168 are defined on the distal portion of the interior surface of cap 122.

Figure 20:
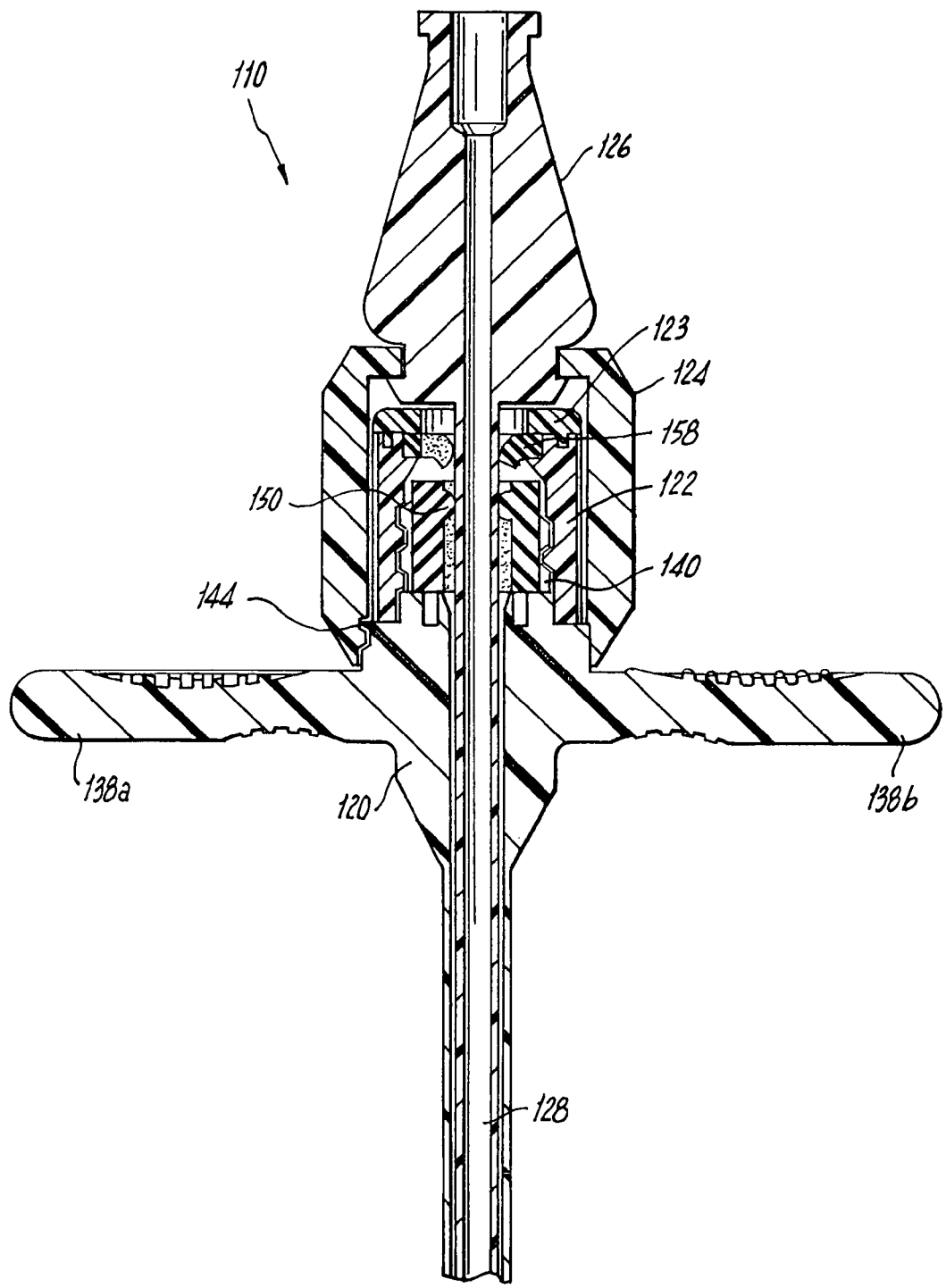
FIG. 20 is a cross sectional view of the vascular introducer of FIG. 13, illustrating the locking collar, sealing cap, dilator handle and dilator secured on the hub portion in a configuration which prevents blood flow through the hemostatic valve and impedes axial movement of the dilator relative to the hub portion through compression of the hemostatic valve against the dilator within the hub portion of the assembly.

FIG. 20 illustrates vascular assembly 110 wherein sealing cap 122 is fully (i.e., as far in the distal direction as possible) threaded onto threads 146 on proximal end portion 140 of hub 120, and locking collar 124 is disposed over cap 122 and fully threaded onto threads 144 on proximal end portion 140 of hub 120. Dilator 128 extends through introducer 110 contacting trocar seal 158 in sealing cap 122, and as explained below, contacting half-rings 153a and 153b of sealing ring 150.

In this configuration, locking collar 124 is fully threaded onto hub 120 preferably by twisting clockwise, which moves both locking collar 124 and sealing cap 122 distally relative to proximal end portion 140. Thus, sealing cap 122 bears down on axial tabs 148 causing a chain reaction of radially inward motion starting with axial tabs 148 and then progressing to both sealing tube halves 150a and 150b. The radial inward position of sealing tube halves 150a and 150b results in contact between half-rings 153a and 153b on tube halves 150a and 150b and dilator 128 which impedes axial movement of dilator 128 and restricts blood flow from exiting hub 120 in the proximal direction.

Figure 21:
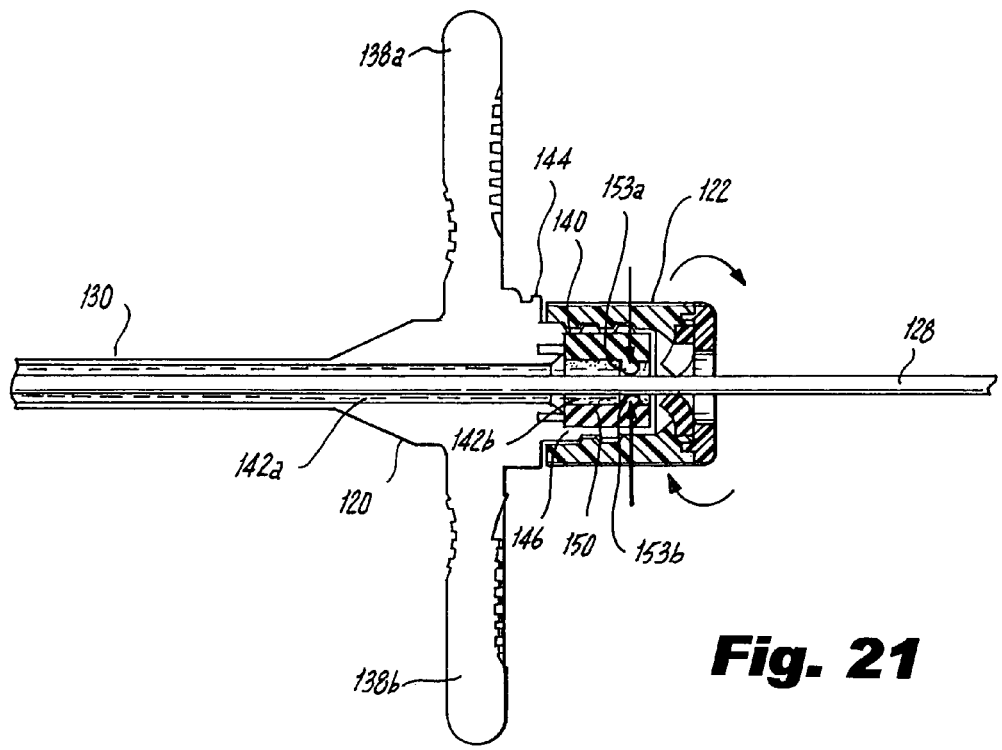
FIG. 21 is cross sectional close up view of the hub portion of the vascular introducer of FIG. 13, illustrating the manner in which the locking collar, dilator handle and dilator are separated from the hub portion and hemostatic valve formed by the sealing cap member, among other things.

FIG. 21 illustrates the introducer assembly 110 during the process of removing locking collar 124 (not shown) and dilator handle 126 (not shown) along with dilator 128 in the proximal direction away from hub 120. Locking cap 124 can be de-threaded from hub 120 and separated from vascular assembly 110 while sealing cap 122 remains in place. Sealing cap 122 is shown as being completely threaded upon the threaded portion 146 of proximal end portion 140. Thus, pressure is applied to cause a crimping action on proximal end portion resulting in the radially inward movement of sealing tube 150.

In this state, dilator 128 may be moved from axially and separated from introducer assembly 110, although it is somewhat impeded by contact with half-rings 153a and 153b. However, the contact with half-rings 153a and 153b substantially restricts blood flow through hub 120 while dilator 128 is being removed. When dilator 128 is fully separated from introducer 110, blood may flow further proximally than sealing tube 150 but is substantially restricted by trocar seal 158.

Figure 22:
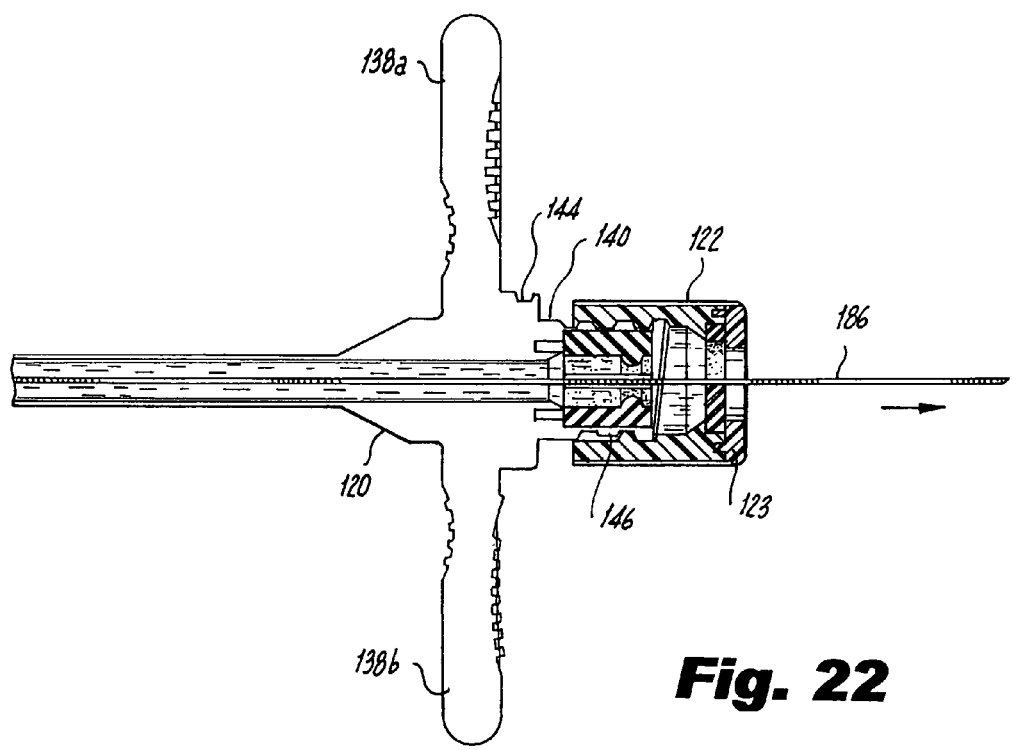
FIG. 22 is cross sectional close up view of the hub portion of the vascular introducer of FIG. 13 without the locking collar, dilator handle and dilator, illustrating the manner in which a guidewire extends through the hub portion and hemostatic valve.

As shown in FIG. 22, dilator 128 has been removed, revealing guidewire 186 which extends through introducer assembly 110 in its place. Cap 122 has been de-threaded along threaded portion 146 on proximal end portion 140, which releases the crimping action and pressure placed on proximal end portion 140, allowing sealing tube 150 to move radially outward to a rest position. In this position, blood can flow freely through axial bore 142b and 142a of hub 120 without being impeded by annular half-rings 153a and 153b. Trocar seal 158 on cap 122 restricts any blood flow from exiting introducer 110.

Figure 23:
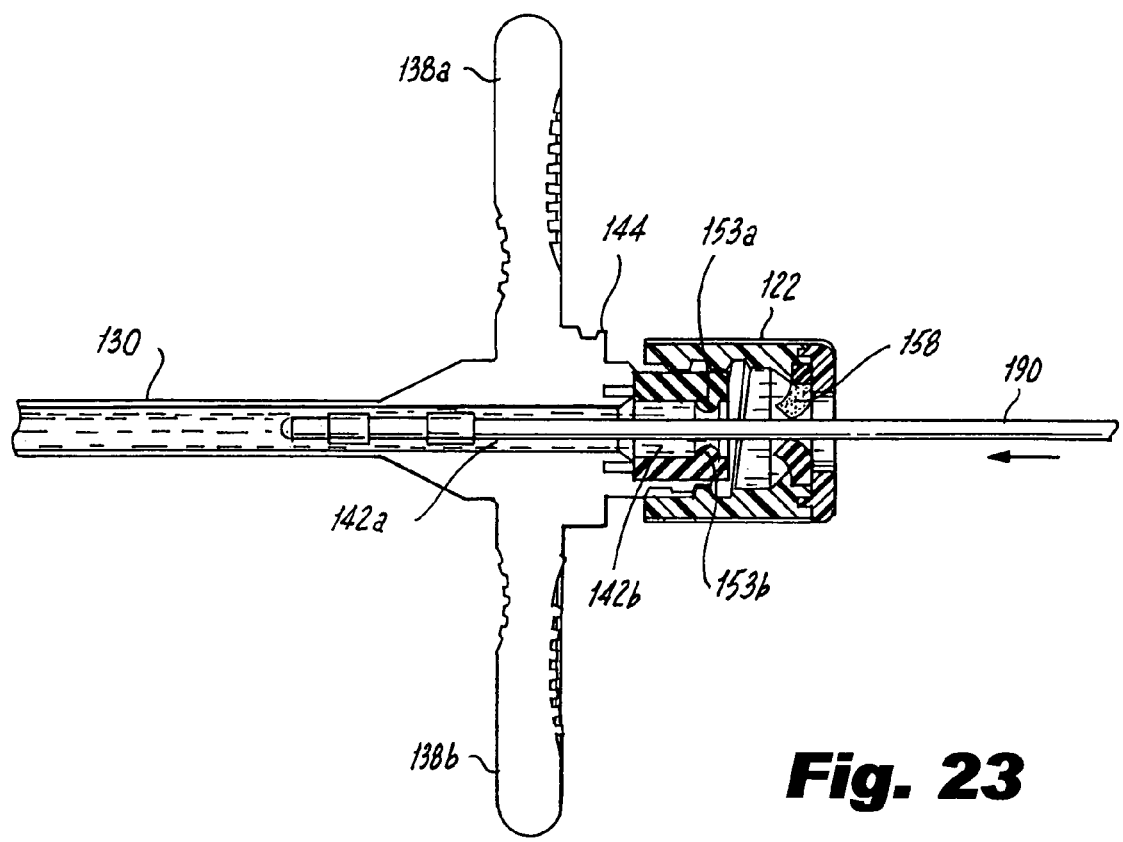
FIG. 23 is cross sectional close up view of the hub portion of the vascular introducer of FIG. 13, without the locking collar, dilator handle and dilator, illustrating the sealing cap member in a configuration which releases the radially inward pressure on the sealing members for facilitating insertion of an endocardial lead through the hub portion.
Figure 24:
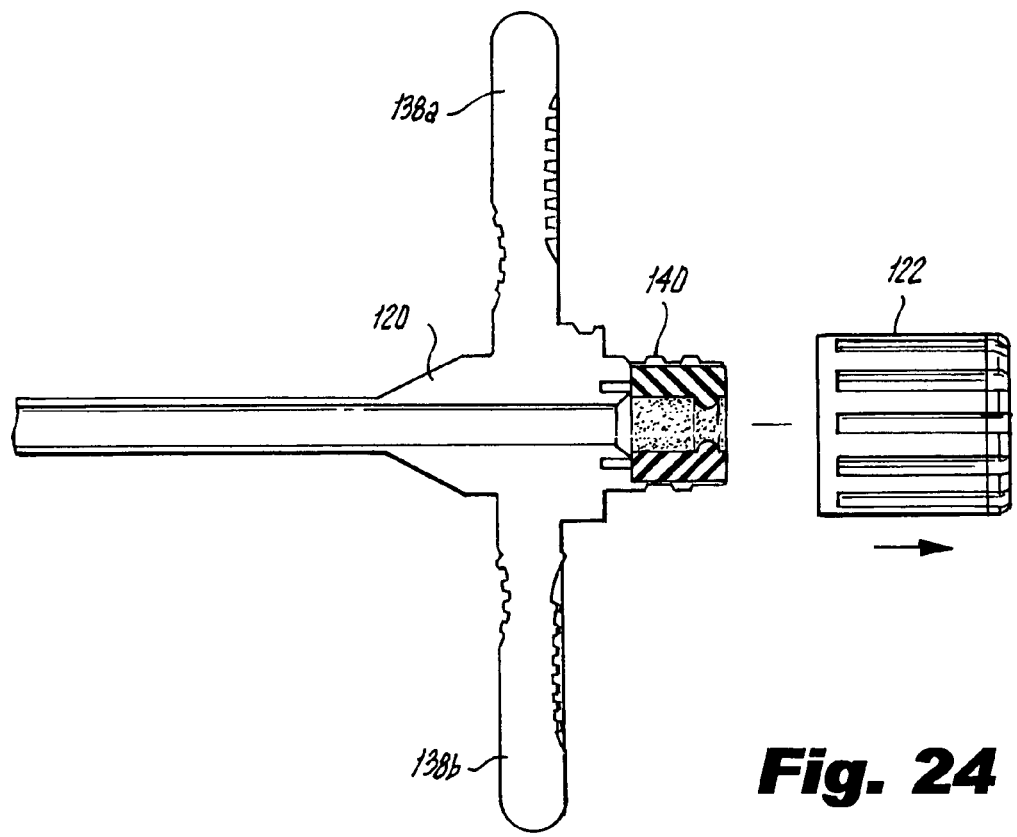
FIG. 24 is cross sectional close up view of the hub portion of the vascular introducer of FIG. 13, without the locking collar, dilator handle and dilator, illustrating the separation of the sealing cap member from the hub portion.

Once guide wire 186 has been separated from introducer 110, introducer 110 can be used to insert devices or equipment intravenously through the axial bores in sealing cap 122, hub 120 and lumen 130, such as endocardial lead 190 as shown in FIG. 23. Sealing cap 122 can be fully de-threaded and removed from proximal end portion 140 to permit blood to flow through introducer 110 without restriction. In addition, once sealing cap 122 is removed, the remaining introducer 110 can be split by pulling apart handles 138a and 138b in the manner described with regard to introducer assembly 10 of the previous embodiment.

Figure 25:
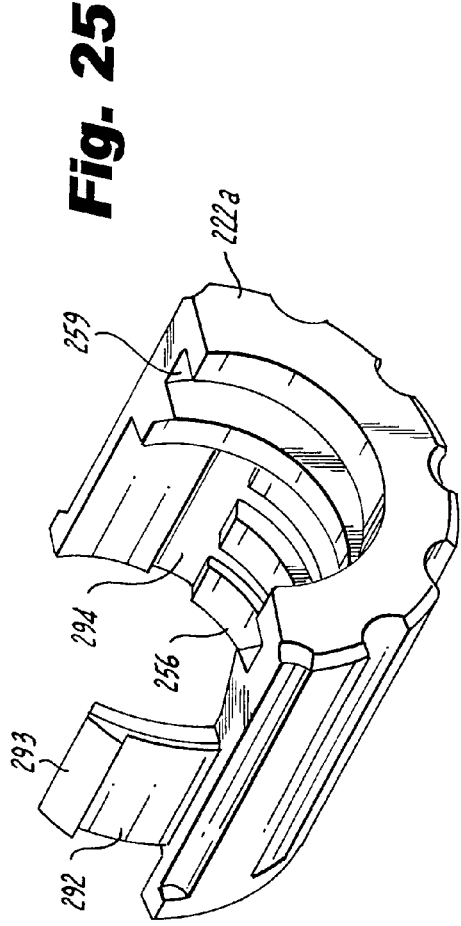
FIG. 25 is a perspective view of one part of a two-part splitable sealing cap member constructed in accordance with another preferred embodiment of the present invention, illustrating the interlocking features, among other things.
Figure 26:
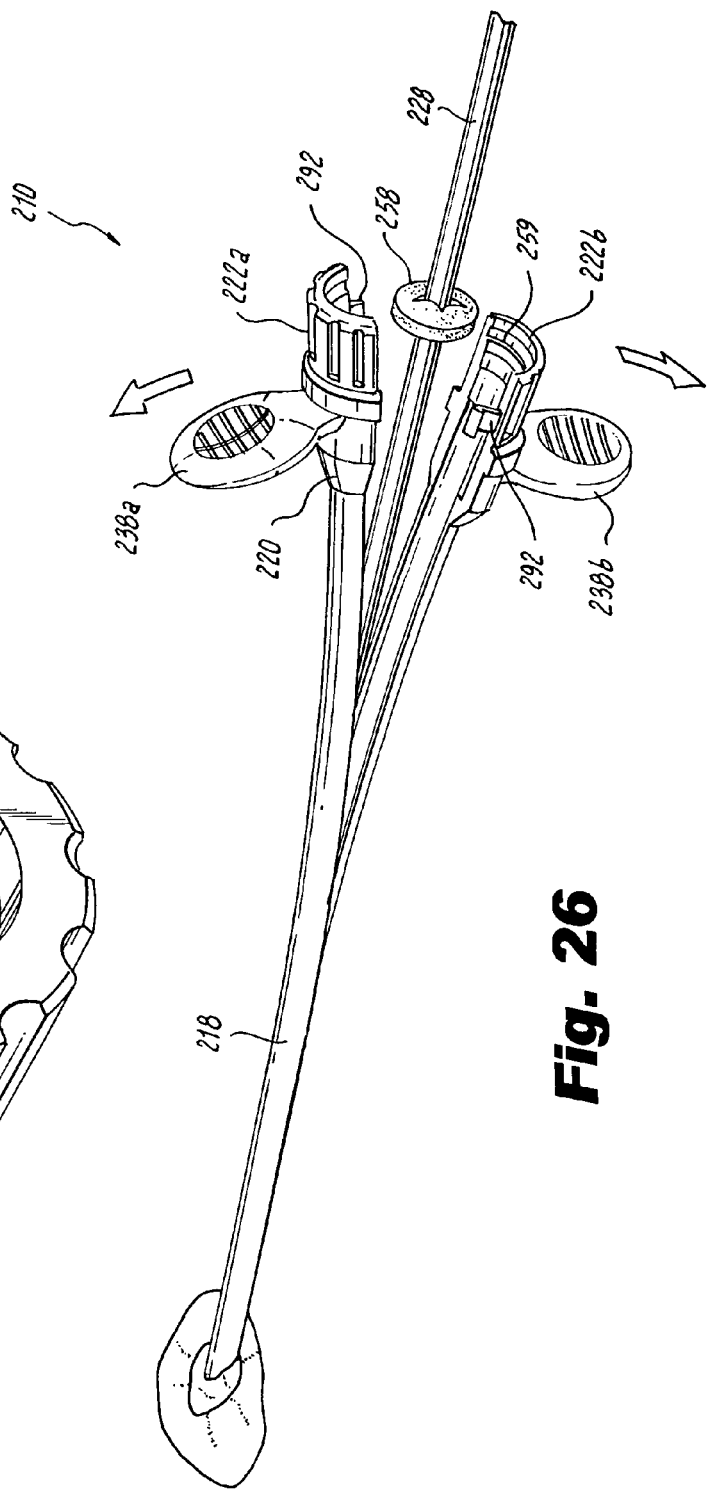
FIG. 26 is a perspective view of a vascular introducer featuring the splitable sealing cap member of FIG. 25, illustrating the manner in which the introducer and sealing cap member can be slit together leaving the trocar seal on the dilator.

In another embodiment, a vascular introducer constructed in accordance with the present invention can include a splitable sealing cap 222 as illustrated in FIGS. 25-26. Vascular introducer 210 includes a sealing cap 222, which can be split longitudinally to form corresponding symmetrical halves 222a and 222b.

Each half sealing cap 222a and 222b includes a circumferentially projecting tab 292 with a ramped end portion 293 thereon. A receiving portion 294 is defined on each half sealing cap 222a and 222b for engaging the projecting tab 292 and ramped end portion 293 of the other sealing cap halves 222a or 222b when cap 222 is assembled. A threaded portion 256 is formed in the interior surface of sealing cap 222 by assembling half caps 222a and 222b. Threads 256 are configured to be engage a threaded portion 246 (not shown) on proximal end portion 240 (not shown). A trocar seal 258 is secured within a groove 259 defined on the interior surfaces of both sealing cap halves 222a and 222b proximally adjacent threaded portion 256.

Sealing cap 222 functions similarly to the previous embodiments to actuate the sealing feature associated with introducer 210 of the present invention. By threading sealing cap 222 onto proximal end portion 240, seal 250 contacts dilator 228 to prevent blood flow proximally through introducer 210. By de-threading sealing cap 222, the flow of blood is permitted through proximal end portion 240 but is stopped by trocar seal 258 of sealing cap 222.

Introducer 210 can be split while sealing cap 222 is in place, provided locking collar 224 (not shown) along with dilator handle 226 (not shown) are removed from introducer 210 prior thereto. As shown in FIG. 26, with sealing cap 222 securely threaded on hub 220 of introducer 210, ramped ends 293 of the sealing cap halves 222a and 222b can be disengaged from their respective receiving portions 294 by pulling handles 238a and 238b in opposing directions. Sealing cap 222 divides into halves 222a and 222b and is thus split along with hub 220 and lumen 218.

FIGS. 27-40 illustrate another embodiment of a vascular introducer assembly constructed in accordance with the present invention and generally designated by the reference numeral 310. This embodiment includes a threaded ring 322 having a trocar seal 358 at its proximal end, as shown in FIG. 32.

Figure 27:
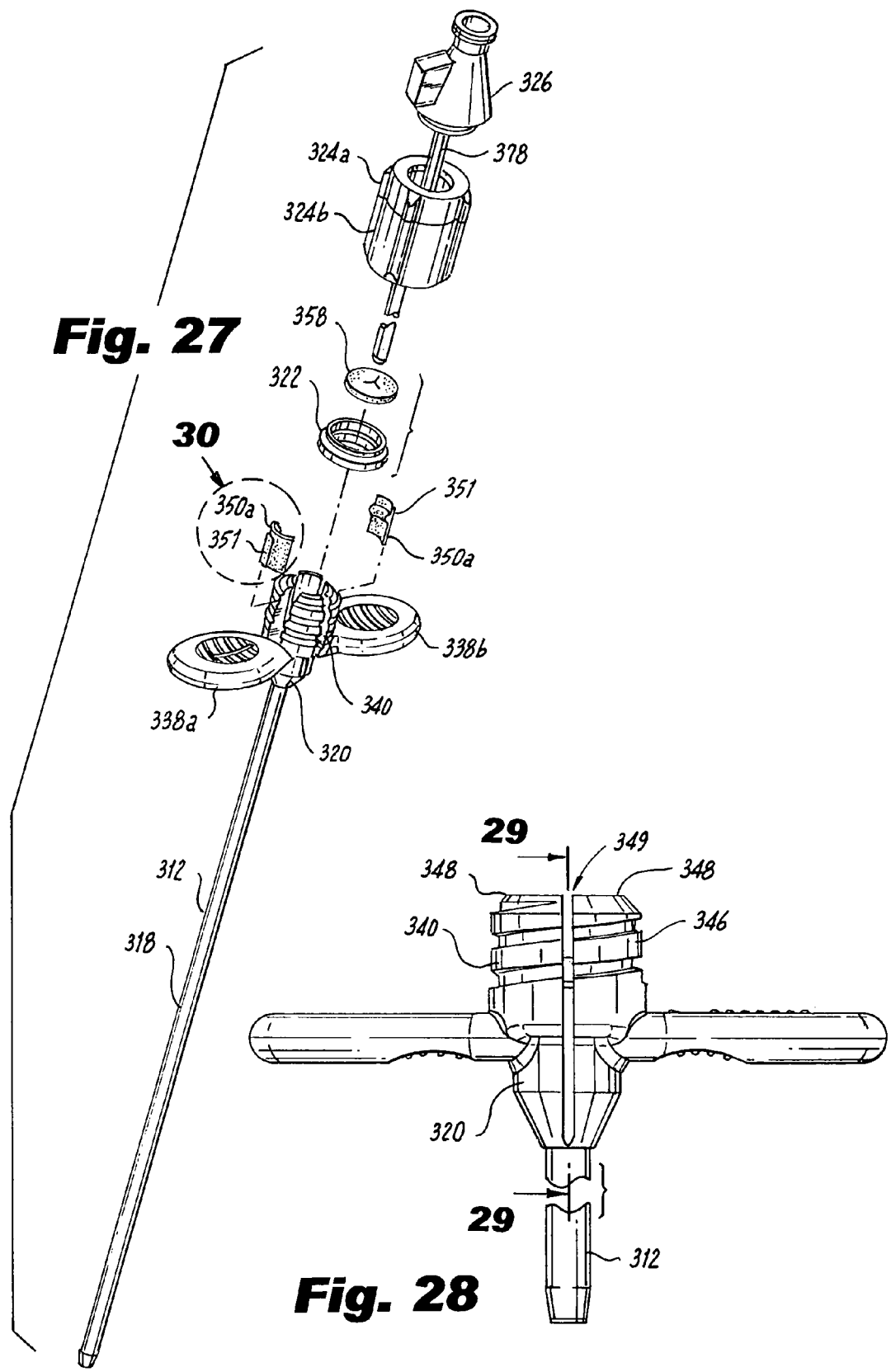
FIG. 27 is an exploded perspective view of a vascular introducer assembly constructed in accordance with another preferred embodiment of the subject invention with parts separated for ease of illustration.
Figure 28:
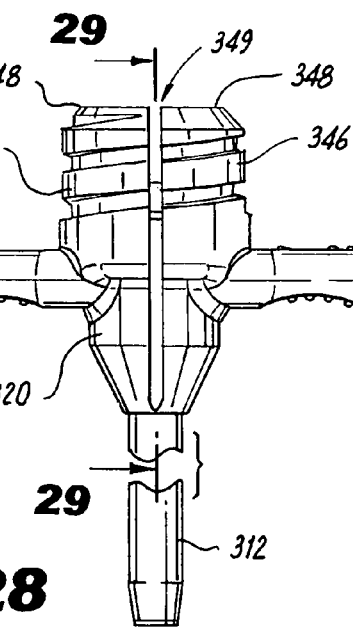
FIG. 28 is an enlarged front view of the hub portion of the vascular introducer assembly of FIG. 27, illustrating the larger diameter proximal end portion of the hub portion, among other things.

Threaded ring 322 is approximately the same diameter as proximal end portion 340. As shown in FIG. 27, sealing half-pipes 350a and 350b are inserted in axial bore 342b of proximal end portion 340 before threaded ring 322 is seated thereon. Proximal end portion 340 is of a larger diameter than in previous embodiments and includes a funnel-like opening in axial bore 342b, as shown in FIG. 29. Proximal end portion 340 also includes four axial slots 349 defining four axial projections 348 making up the proximal end portion 340 to enhance the range of radially inward movement, among other things.

As shown in FIG. 33, threaded ring 322 includes threads on its exterior that can match with threads 346 on proximal end portion 340. This feature allows the combination of threaded ring 322 and proximal end portion 340 to be simultaneously engaged with threads 368 defined on the interior surface of locking collar 324, as can be best viewed in FIGS. 36-40.

In this embodiment, locking collar 324 is splitable and defines a proximal end portion 324a and a distal end portion 324b, as shown in FIGS. 34 and 35. Proximal end portion 324a, which is connected with dilator handle 326, and a distal end portion 324b, which includes threads 368 defined on its interior surface. Proximal portion 324a of collar 324 can be separated from distal portion 324b with dilator handle 326 attached thereto. Distal portion 324b can be threaded onto threaded ring 322 and proximal end portion 340 of hub 320 without proximal portion 324a.

Figure 36:
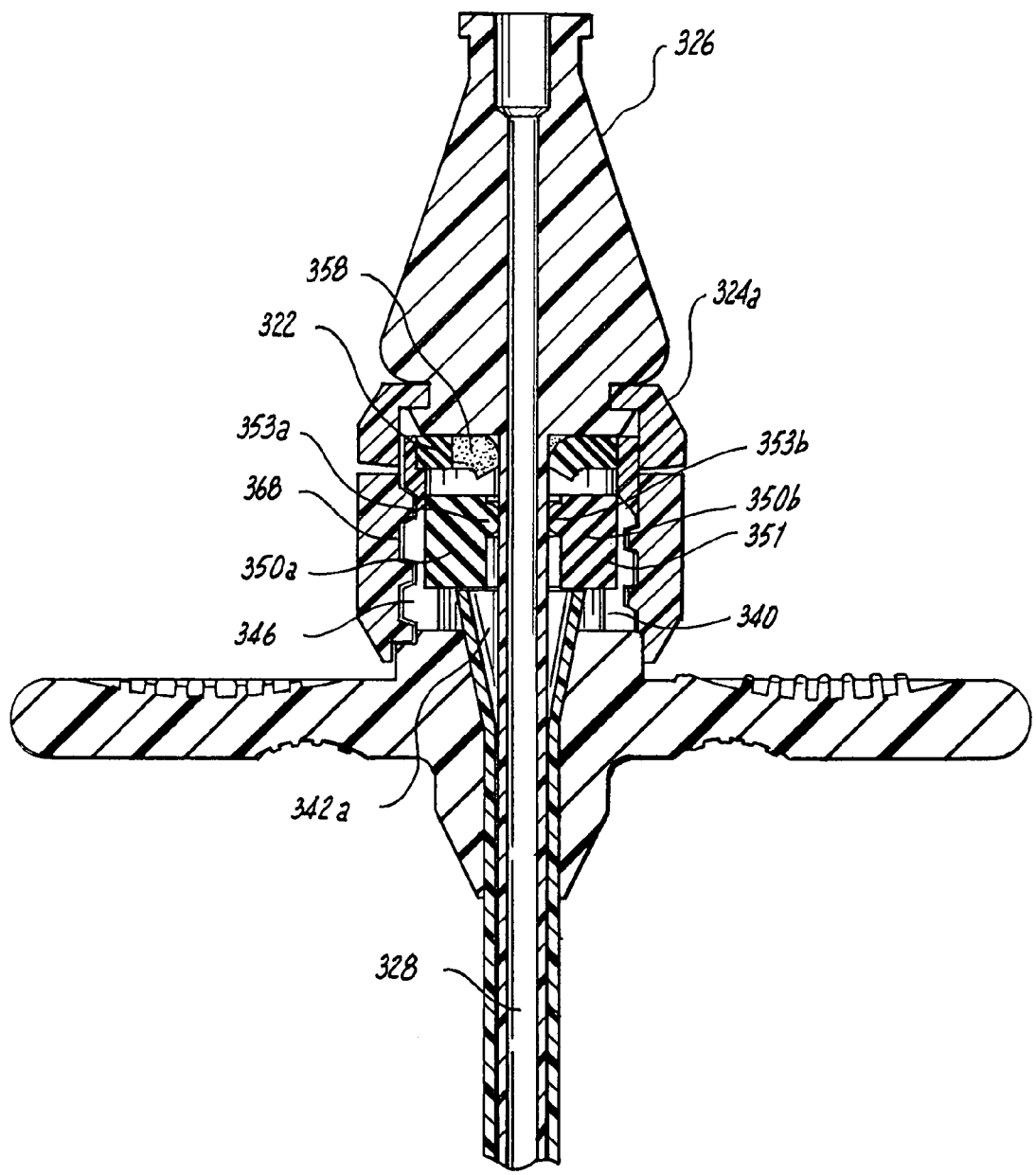
FIG. 36 is a cross sectional view of the hub portion of the vascular introducer of FIG. 27, wherein the dilator handle is mounted on the non-threaded portion of the locking collar, and the threaded portion of the locking collar is fully threaded onto the proximal end portion of the hub portion and over the annular member with the trocar seal, among other things.
Figure 37:
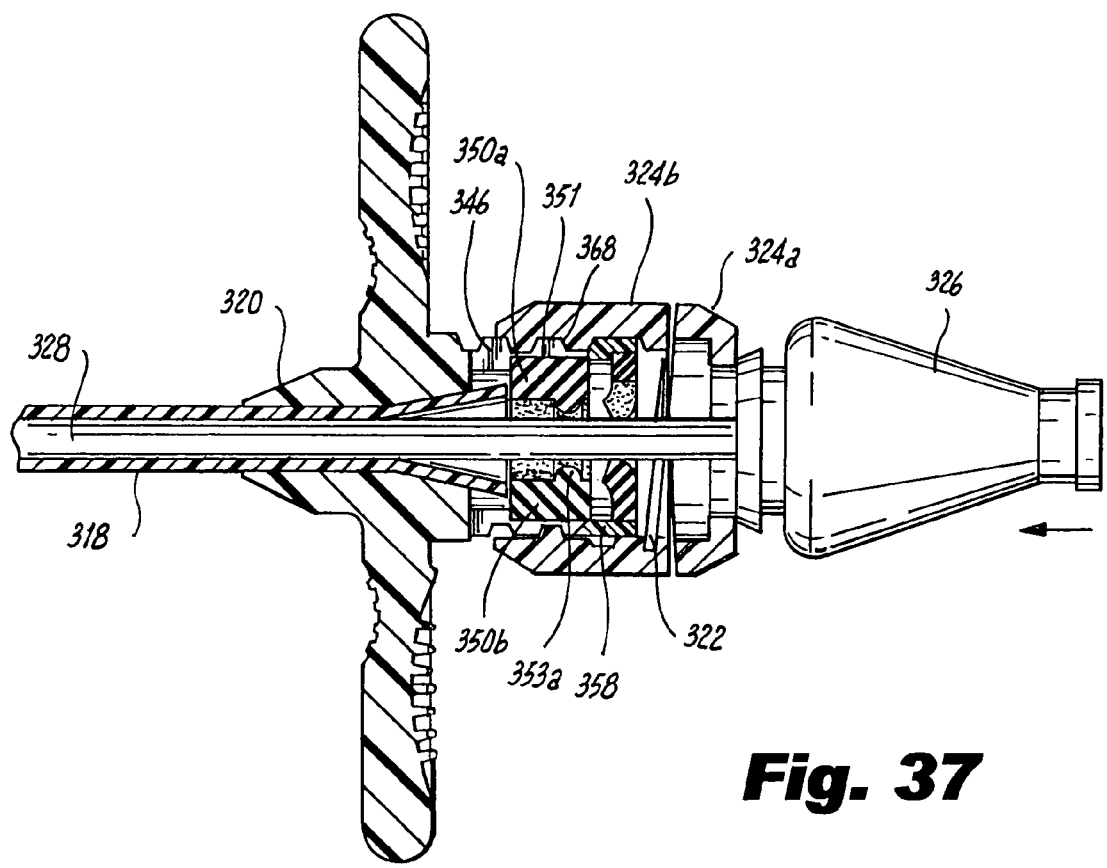
FIG. 37 is a partial cross sectional view of the hub portion of the vascular introducer of FIG. 27, wherein the dilator handle is mounted on the non-threaded portion of the locking collar, and the threaded portion of the locking collar is de-threaded on the proximal end portion of the hub portion and radially inward pressure on the annular seal is not applied, among other things.
Figure 38:
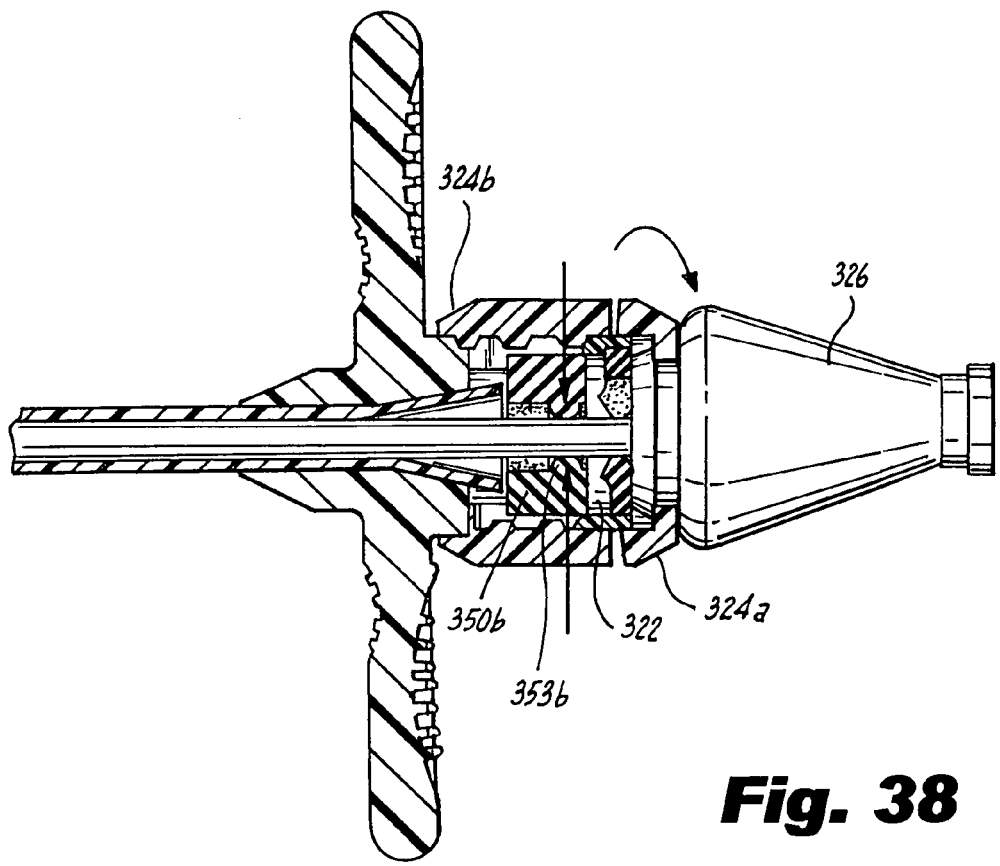
FIG. 38 is a partial cross sectional view of the hub portion of the vascular introducer of FIG. 27, wherein the dilator handle is mounted on the non-threaded portion of the locking collar, and as illustrated by the arrows, radially inward pressure on the annular seal is applied by the threaded portion of the locking collar being fully threaded onto the proximal end portion of the hub portion, among other things.

In use, threading collar 324 on threaded ring 322 and proximal end portion 340 applies a crimping action to sealing tube 350 therein, as can be best viewed in FIGS. 36 and 38. By being secured against proximal end portion 340, threaded ring 322 bears down on proximal end portion 340 when locking collar 324 is threaded on proximal end portion 340. This results in the radially inward movement of axial projections 348 of proximal end portion 340 causing inner rings 353a and 353b of seal 350 to contact dilator 328. The contact between rings 353a and 353b and dilator 328 forms a seal that prevents blood flow from exiting proximally through introducer 310. The crimping action can be released by de-threading collar 324 on proximal end portion 340, as shown in FIG. 37.

Thus, in this embodiment, collar 324 generally serves as both a sealing cap and a locking collar for dilator 328 and dilator handle 326, in that threading or de-threading collar 324 either seals or releases the seal created by cylindrical seal 350 and inner half rings 353a and 353b, among other things.

Figure 39:
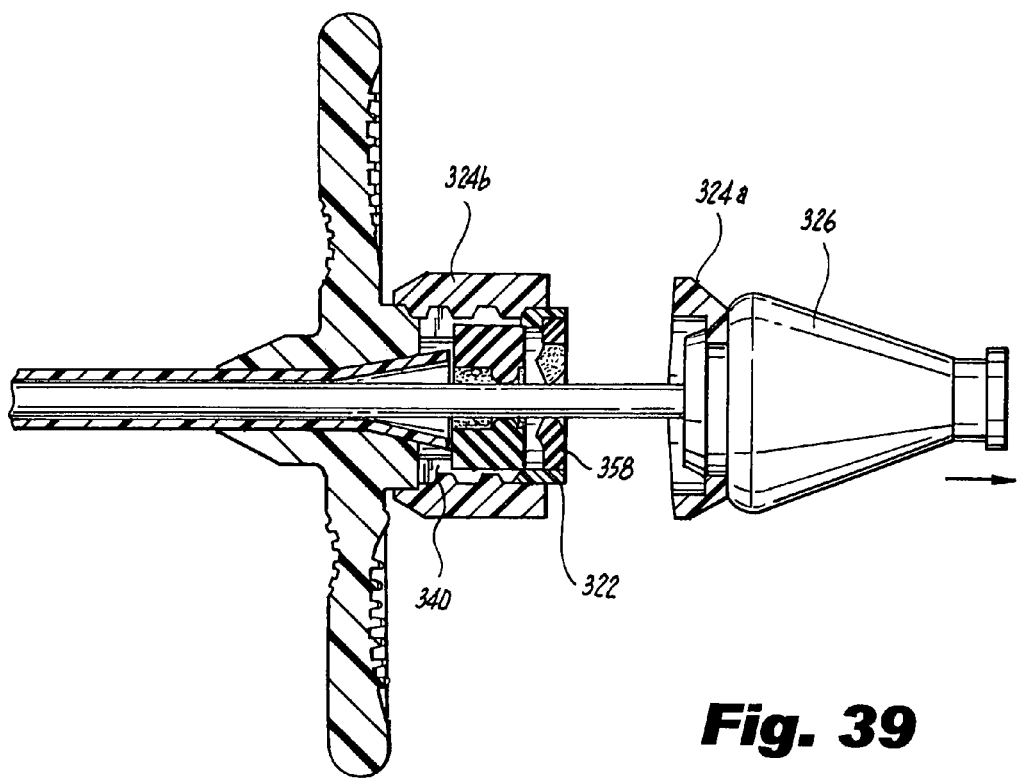
FIG. 39 is a partial cross sectional view of the hub portion of the vascular introducer of FIG. 27, illustrating the manner in which the locking collar can be separated to remove the dilator without removing the annular member with the trocar seal or de-threading the threaded portion of the locking collar from the proximal end portion of the hub portion, which remain in place to maintain the hemostatic valve in the closed position, among other things.
Figure 40:
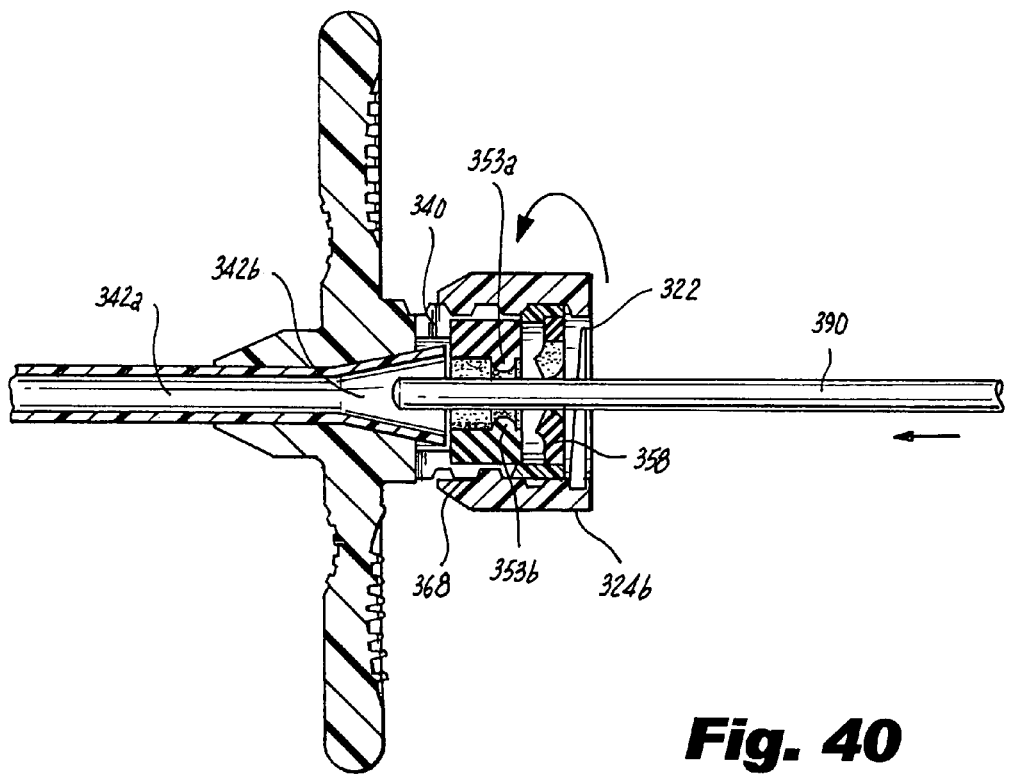
FIG. 40 is a partial cross sectional view of the hub portion of the vascular introducer of FIG. 27, illustrating the manner in which the threaded portion of the locking collar can actuate the hemostatic valve so that the valve can alternate between an open and closed position and an endocardial lead being inserted through the trocar in the annular member which remains in place on the proximal end portion.

Furthermore, as shown in FIG. 39-40, distal end portion 324b of collar 324 can actuate the crimping action without proximal end portion 324a.

As can be viewed in FIG. 39, dilator handle 326 and dilator 328 may be removed from assembly 310 by separating proximal portion 324a of from distal portion 324b of locking collar 324. Distal end portion 324b of collar 324 can remain secured on proximal end portion 340 as a functioning actuator for the seal in proximal end portion 340 provided dilator 328 remains within introducer 310. If dilator 328 is separated from introducer 310, threaded ring 322 with trocar seal 358 remains in place adjacent proximal end portion 340 of hub 320 to prevent blood from escaping introducer 310, as shown clearly in FIGS. 39-40.

Also, as shown in FIG. 40, introducer 310 can be used to insert devices or equipment intravenously through lumen 130, such as an endocardial lead 390, by de-threading distal collar portion 324b along proximal end portion 340 and threaded ring 322, which releases the crimping action on proximal end portion 340, but allows devices to be inserted through trocar seal 358 and the larger diameter proximal end portion 340.

While the invention has been described with respect to preferred embodiments, those skilled in the art will readily appreciate that various changes and/or modifications can be made to the invention with departing from the spirit or scope of the invention.

What is claimed is:

1. A vascular introducer assembly comprising:
   a) an elongated sheath having opposed proximal and distal end portions and having an axial lumen extending therethrough for accommodating a dilator;
   b) a flexible and pliable axial hub operatively associated with the proximal end portion of the sheath and having an axial bore extending therethrough in communication with the axial lumen of the sheath and further including longitudinally extending slots for dividing the hub along a longitudinal axis thereof;
   c) a cylindrical seal supported within the axial bore of the hub; and
   d) a rotatable actuator for moving the hub radially inward to radially compress the cylindrical seal supported therein.

2. A vascular introducer assembly as recited in claim 1, wherein the rotatable actuator comprises an annular actuator ring threadably associated with an exterior surface of the hub.

3. A vascular introducer assembly as recited in claim 2, wherein the actuator ring is operatively engaged within a selectively rotatable actuation collar.

4. A vascular introducer assembly as recited in claim 3, wherein the actuation collar includes a distal portion and a proximal portion, and wherein the actuator ring is operatively engaged within the distal portion of the actuation collar.

5. A vascular introducer assembly as recited in claim 4, wherein the actuation collar includes a separable connection between the proximal and distal portions thereof for separating the proximal portion of the actuation collar from the distal portion of the actuation collar.

6. A vascular introducer assembly as recited in claim 5, wherein the proximal portion of the actuation collar is operatively engaged with a proximal end portion of a dilator accommodated within the axial lumen of the sheath.

7. A vascular introducer assembly as recited in claim 2, wherein a trocar seal is disposed within the actuator ring.

8. A vascular introducer assembly as recited in claim 1, wherein the cylindrical seal is divided into semi-cylindrical half sections.

9. A vascular introducer assembly as recited in claim 8, wherein each semi-cylindrical half section of the cylindrical seal includes a radially outwardly extending tab for engaging the hub and a radially inwardly projecting portion of an integral annular ring seal.

10. A vascular introducer assembly as recited in claim 1, wherein the rotatable actuator comprises a selectively rotatable cylindrical actuator cap threadably associated with an exterior surface of the hub.

11. A vascular introducer assembly as recited in claim 10, wherein a trocar seal is disposed within the actuator cap.

12. A vascular introducer assembly as recited in claim 1, wherein the sheath includes longitudinally extending score lines for dividing the sheath along a longitudinal axis thereof.

13. A vascular introducer assembly as recited in claim 1, wherein the hub includes diametrically opposed handle portions.

14. A vascular introducer assembly as recited in claim 1, wherein the actuator cap includes releasable engagement tabs for dividing the cap along a longitudinal axis thereof.

15. A vascular introducer assembly comprising:
   a) an elongated sheath having opposed proximal and distal end portions and having an axial lumen extending therethrough for accommodating a dilator;
   b) a flexible and pliable axial hub operatively associated with the proximal end portion of the sheath and having an axial bore extending therethrough in communication with the axial lumen of the sheath and further including longitudinally extending slots for dividing the hub along a longitudinal axis thereof;
   c) a cylindrical seal retained within the axial bore of the hub; and
   d) a selectively rotatable cylindrical actuator cap threadably associated with the hub for selectively compressing the hub in a radially inward direction to radially compress the cylindrical seal retained therein.

16. A vascular introducer assembly as recited in claim 15, wherein the sheath includes longitudinally extending score lines for dividing the sheath along a longitudinal axis thereof.

17. A vascular introducer assembly as recited in claim 15, wherein the cylindrical seal is divided into semi-cylindrical half sections each having a radially outwardly extending tab for engaging the hub and a radially inwardly projecting portion of an integral annular ring seal.

18. A vascular introducer assembly as recited in claim 15, wherein the actuator cap includes releasable engagement tabs for dividing the cap along a longitudinal axis thereof.

19. A vascular introducer assembly as recited in claim 15, wherein a trocar seal is retained within the actuator cap.

20. A vascular introducer assembly comprising:
   a) an elongated sheath having opposed proximal and distal end portions and having an axial lumen extending therethrough for accommodating a dilator;
   b) a flexible and pliable axial hub operatively associated with the proximal end portion of the sheath and having an axial bore extending therethrough in communication with the axial lumen of the sheath and further including longitudinally extending slots for dividing the hub along a longitudinal axis thereof;
   c) a cylindrical seal retained within the axial bore of the hub; and
   d) a selectively rotatable annular actuator ring threadably associated with the hub for selectively compressing the hub in a radially inward direction to radially compress the cylindrical seal retained therein.

21. A vascular introducer assembly as recited in claim 20, wherein a trocar seal is disposed within the actuator ring.

22. A vascular introducer assembly as recited in claim 21, wherein the actuator ring is operatively engaged within a selectively rotatable actuation collar.

23. A vascular introducer assembly as recited in claim 22, wherein the actuation collar includes a distal portion and a proximal portion, and wherein the actuator ring is operatively engaged within the distal portion of the actuation collar.

24. A vascular introducer assembly as recited in claim 23, wherein the actuation collar includes a separable connection between the proximal and distal portions thereof for separating the proximal portion of the actuation collar from the distal portion of the actuation collar.

25. A vascular introducer assembly as recited in claim 24, wherein the proximal portion of the actuation collar is operatively engaged with a proximal end portion of a dilator accommodated within the axial lumen of the sheath.

26. A vascular introducer assembly as recited in claim 20, wherein the sheath includes longitudinally extending score lines for dividing the sheath along a longitudinal axis thereof.

27. A vascular introducer assembly as recited in claim 20, wherein the cylindrical seal is divided into semi-cylindrical half sections each having a radially outwardly extending tab for engaging the hub and a radially inwardly projecting portion of an integral annular ring seal.

* * * * *